United States Patent [19]
Yang et al.

[11] Patent Number: 5,854,028
[45] Date of Patent: Dec. 29, 1998

[54] COMPOSITIONS COMPRISING IL-11 AND METHODS OF MAKING AND USING IL-11

[75] Inventors: Yu-Chung Yang, Indianapolis, Ind.; Frances K. Bennett, Melrose; Stephan R. Paul, Boston, both of Mass.

[73] Assignee: Genetics Institute, Inc., Cambridge, Mass.

[*] Notice: The term of this patent shall not extend beyond the expiration date of Pat. No. 5,700,664.

[21] Appl. No.: 814,459

[22] Filed: Mar. 10, 1997

Related U.S. Application Data

[60] Division of Ser. No. 949,516, Nov. 19, 1992, Pat. No. 5,700,664, which is a continuation-in-part of Ser. No. 526,474, May 21, 1990, Pat. No. 5,215,895, which is a continuation-in-part of Ser. No. 441,100, Nov. 22, 1989, abandoned.

[51] Int. Cl.⁶ .......................... C12N 15/63; C07K 14/54; A61K 38/20
[52] U.S. Cl. ................. 435/69.52; 435/41.1; 435/325; 435/252.3; 435/320.1; 530/351; 536/23.1; 536/23.5; 424/85.2; 424/198.1; 514/8; 514/12; 514/885; 514/887
[58] Field of Search ................. 424/85.1, 85.2, 424/198.1; 514/2, 8, 12, 887, 885; 435/69.52, 71.1, 325, 252.3, 320.1; 530/351; 536/23.1, 23.5

[56] References Cited

U.S. PATENT DOCUMENTS 4,863,727  9/1989  Zimmerman et al. ................. 424/85.2

FOREIGN PATENT DOCUMENTS 5-71866  3/1993  Japan .

OTHER PUBLICATIONS

Bourie et al. (1990) Science vol. 247 pp. 1306–1310.
Callard & Gearing (1994) The Cytokine Facts Book, Academic Press Limited, p. 39.
Balkwill, et al., Immunology Today 10(9):299–304 (1989).
Cate, et al., Cell 45:685–98 (1986).
Clark, et al., Science 236:1229–1237 (1987).
Du, Blood 78(Suppl):403a (1991) (G1 5174A–Div).
Fiorentino, et al., J. Exp. Med. 170:2081–95 (1989) (Abstract only).
Geiger, et al., Eur. J. Biochem. 175:181–86 (1988).
Geisow, Biotech. 9:921–924 (1991).
Giannotti, et al., Lymphokine Research 9(4):601(4.5)(1990).
Goldman, J. Cell Biochem. Supp. 116C:74 (1992).
Hanemaaijer, et al., Eur. J. Biochem. 174:593–99 (1988).
Kimimiya, et al., J. Bacteriol. 170:1800–11 (1988).
McGeoch, et al., Nucleic Acid Res. 14:1727–45 (1986).
Moore, et al., Science 248:1230–34 (1990).
Musashi, Blood 78:1448–51 (1991).
Musashi, Proc. Natl. Acad. Sci. 88:765–69 (1991).
Nordan, et al., Science 233:566–569 (1986).
Oppenhein, et al., Immunophysiology–The Role of Cells and Cytokines in Immunity and Inflation, p. 167 (1990).
Paul, et al., Proc. Natl. Acad. Sci. USA 87:7512–7516 (1990).
Quesiaux, Blood 80(5):1218–23 (1992).
Quesniaux, J. Cell Biochem. Supp. 15F:129 (1991).
Rall, et al., J. Clin. Invest. 83:1095–1101 (1989).
Reeck, et al., Cell 50:667 (1987).
Sausville, et al., J. Biol. Chem 260:10236–41 (1985).
Selten, et al., Cell 46:603–11 (1986).
Williams, et al., Mol. Cell Biol. 8:3064–3071 (1988).
Wong, et al., Immunology Today 9(5):137–139 (1988).
Yin, J. Exp. Med. 175:211–216 (1992).
Zalacian, et al., Nucleic Acid Res. 14:1565–81 (1986).

*Primary Examiner*—Stephen Walsh
*Assistant Examiner*—Prema Mertz
*Attorney, Agent, or Firm*—Steven R. Lazar; Maureen C. Meinert

[57] ABSTRACT

A novel mammalian cytokine, IL-11, and processes for producing it are disclosed. IL-11 may be used in pharmaceutical preparations for stimulating and/or enhancing cells involved in the immune response and cells involved in the proper functioning of the hematopoietic system.

24 Claims, 2 Drawing Sheets

COMPOSITIONS COMPRISING IL-11 AND METHODS OF MAKING AND USING IL-11

This application is a divisional of application Ser. No. 07/949,516, filed Nov. 19, 1992 now U.S. Pat. No. 5,700,664; which is a continuation in part of U.S. Ser. No. 07/526,474, filed May 21, 1990, now U.S. Pat. No. 5,215,895; which, in turn is a continuation in part of U.S. Ser. No. 07/441,100 filed Nov. 22, 1989 and now abandoned.

The present invention relates to a novel cytokine that stimulates the function of cells of the immune and hematopoietic systems, and to processes for obtaining the factor and producing it by recombinant genetic engineering techniques.

BACKGROUND OF THE INVENTION

A growing family of regulatory proteins that deliver signals between cells of the immune system has been identified. These regulatory molecules are known as cytokines. Many of the cytokines have been found to control the growth and development, as well as the biological activities of cells of the hematopoietic and immune systems. These regulatory molecules include all of the colony-stimulating factors (e.g., GM-CSF, G-CSF, M-CSF, and multi CSF or interleukin-3), the interleukins (IL-1 through IL-9), the interferons (alpha, beta and gamma), the tumor necrosis factors (alpha and beta), erythropoietin, macrophage inhibitory proteins, the tumor growth factors and leukemia inhibitory factor (LIF). These cytokines exhibit a wide range of biological activities with target cells from bone marrow, peripheral blood, fetal liver, and other lymphoid or hematopoietic organs. See, e.g., F. R. Balkwill and F. Burke, *Immunology Today*, 10(9):299 (1989); G. Wong and S. Clark, *Immunology Today*, 9(5):137 (1988); and S. C. Clark and R. Kamen, *Science*, 236:1229–1237 (1987).

The biochemical and biological identification and characterization of certain cytokines was hampered by the small quantities of the naturally occurring factors available from natural sources, e.g., blood and urine. Many of the cytokines have recently been molecularly cloned, heterologously expressed and purified to homogeneity. Several of these purified factors have been found to demonstrate regulatory effects on the hematopoietic and immune systems in vivo, including GM-CSF, M-CSF, G-CSF, IL-1, IL-2, IL-3, IL-6, IL-7, TNF, the interferons and erythropoietin.

There remains a need in the art for additional proteins purified from their natural sources or otherwise produced in homogeneous form, which are capable of stimulating or enhancing immune responsiveness and hematopoietic cell development, which are suitable for pharmaceutical use.

SUMMARY OF THE INVENTION

In one aspect the present invention provides a novel mammalian cytokine, called IL-11, which is substantially free from other mammalian proteins. This protein may be produced by recombinant genetic engineering techniques. It may also be purified from cell sources producing the factor naturally or upon induction with other factors. IL-11 may also be synthesized by chemical techniques, or a combination of the above-listed techniques.

Active, mature mammalian IL-11 is an approximately 178 amino acid protein, characterized by an apparent molecular weight of approximately 20 kd, as determined by analyzing $^{35}S$ methionine labelled supernatant fluid derived from IL-11 cDNA transfected COS-1 cells on sodium dodecylsulfate polyacrylamide gel electrophoresis. The calculated molecular weight for the mature protein is also approximately 20 kd.

The IL-11 protein of this invention has displayed biological activities in various assays, which indicate its role as a general stimulator of a variety of hematopoietic and immune functions. The IL-11 protein of this invention demonstrates proliferative activity in an IL-6 dependent mouse plasmacytoma cell line, T1165. IL-11 has also demonstrated in preliminary assays, the ability to stimulate, either directly or indirectly, the maturation of B cells. Specifically, IL-11 is believed to stimulate the T cell dependent development of B cells. It has further demonstrated synergy with IL-3 in an assay stimulating megakaryocyte proliferation, but may act on other lineages as well.

Another aspect of the present invention is a DNA sequence that encodes the expression of a mammalian IL-11 protein. This DNA sequence may include an isolated DNA sequence that encodes the expression of a mammalian IL-11 protein as described above. The DNA sequence coding for active IL-11 is characterized as comprising the same or substantially the same nucleotide sequence in Table I or fragments thereof. This DNA sequence may include 5' and 3' mammalian non-coding sequences flanking the IL-11 coding sequence. The DNA sequence may also encode an amino terminal signal peptide. Table I illustrates these non-coding 5' and 3' flanking sequences and a signal sequence of mammalian IL-11 isolated from the primate cell line PU34 and expressed in COS-1 cells.

It is understood that the DNA sequence of this invention may, however, exclude some or all of these flanking or signal sequences. Moreover the DNA sequence of the present invention which encodes a biologically active mammalian IL-11 protein may also comprise DNA capable of hybridizing under appropriate conditions, or which would be capable of hybridizing under said conditions, but for the degeneracy of the genetic code, to an isolated DNA sequence of Table I. Thus, the DNA sequence of this invention may include or contain modifications in the non-coding sequences, signal sequences or coding sequences based on allelic variation, species variation or deliberate modification.

Also provided by the present invention is a recombinant DNA molecule comprising vector DNA add a DNA sequence encoding mammalian IL-11. The DNA molecule provides the IL-11 DNA in operative association with a regulatory sequence capable of directing the replication and expression of IL-11 in a selected host cell. Host cells transformed with such DNA molecules for use in expressing recombinant IL-11 protein are also provided by the present invention.

The DNA molecules and transformed cells of the invention are employed in another aspect, a novel process for producing recombinant mammalian IL-11 protein, or peptide fragments thereof. In this process a cell line transformed with a DNA sequence encoding expression of IL-11 protein or a fragment thereof (or a recombinant DNA molecule as described above) in operative association with a suitable regulatory or expression control sequence capable of controlling expression of the protein is cultured under appropriate conditions permitting expression of the recombinant DNA. The expressed IL-11 protein is then harvested from the host cell or culture medium by suitable conventional means. This claimed process may employ a number of known cells as host cells for expression of the protein. Presently preferred cell lines for producing IL-11 are mammalian cell lines and bacterial cells.

Another aspect of this invention provides pharmaceutical compositions containing a therapeutically effective amount of mammalian IL-11 or of one or more biologically active peptide fragments thereof. These proteins or peptide fragments may be presented in a pharmaceutically acceptable vehicle. These pharmaceutical compositions may be employed, alone or in combination with other suitable pharmaceutical agents, in methods for treating disease states characterized by a deficiency in the number or level of activity of hematopoietic cells. Pharmaceutical compositions containing IL-11 may be also be employed for the treatment of disorders of the immune system, such as immunodeficiencies.

IL-11 containing compositions may be used to stimulate megakaryocyte growth and differentiation in synergy with IL-3. Additional areas of use are in platelet formation, acquired chemotherapeutic or bone marrow related thrombocytopenia. IL-11 is also likely to operate as an effector molecule to improve the function of other cytokines. IL-11 compositions may also be useful in directly or indirectly stimulating the production or function of B cells. Thus IL-11 compositions may be employed in therapies for cancer, the treatment of infections, acceleration of wound healing and in stimulating the immune system in general. IL-11 may also be used in potentiating the immune response to certain antigens, particularly vaccines.

A further aspect of the invention, therefore, is a method for treating these and/or other pathological states by administering to a patient a therapeutically effective amount of IL-11 or a peptide fragment thereof in a suitable pharmaceutical carrier. These therapeutic methods may include administering simultaneously or sequentially with IL-11 or a peptide fragment thereof an effective amount of at least one other cytokine, hematopoietin, interleukin, growth factor, or antibody.

Still another aspect of the present invention are antibodies directed against mammalian IL-11 or a peptide thereof. As part of this aspect, therefore, the invention claims.cell lines capable of secreting such antibodies and methods for their production.

Other aspects and advantages of the present invention are described further in the following detailed description of preferred embodiments of the present invention.

DESCRIPTION OF THE DEPOSITS

Figure 1:
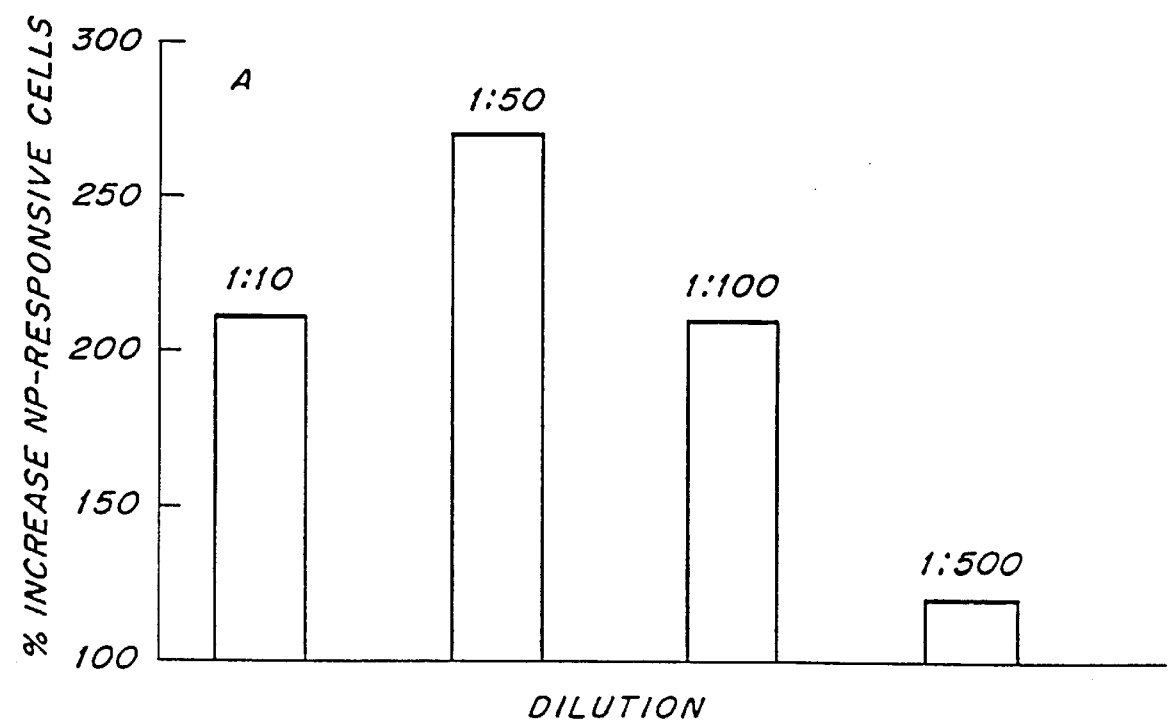
FIG. 1 graphically depicts the enhancement of the development of murine NP-reactive B cells by pC1R6-transfected cos-1 cell conditioned medium in the murine plaque-forming assay.

ATCC 68172 is a deposit of *E. coli* strain HB101 containing the plasmid pPU-34 TRA, which encodes primate IL-11. The strain can be cultured in L broth plus 100 ug/ml ampicillin at 37° C. The strain was deposited on Nov. 14,1989, at the American Type Culture Collection, 12301 Parklawn Drive, Rockville, Md. 20852.

ATCC 68284 is a deposit of *E. coli* strain pHIL10, which contains the plasmid pHIL1013BB, which encodes the human IL-11 DNA. The strain can be cultured in L broth plus 100 ug/ml ampicillin at 37° C. The strain was deposited on Nov. 14, 1989, at the American Type Culture Collection, 12301 Parklawn Drive, Rockville, Md. 20852.

DETAILED DESCRIPTION OF THE INVENTION

The present invention provides a biologically active mammalian cytokine, IL-11, in a form substantially free from association with other mammalian proteins and proteinaceous materials. This protein can be produced via recombinant techniques to enable large quantity production of pure, active IL-11 useful for therapeutic applications. Alternatively, this protein may be obtained as a homogeneous protein purified from a mammalian cell line secreting or expressing it. Further IL-11 or active fragments thereof may be chemically synthesized.

Mammalian IL-11 was initially isolated from a primate cell line developed by placing bone marrow cells from a healthy macaque monkey in long term culture and infecting them with the retrovirus U19-5 [Dr. Roger Cone, Tufts Medical School]. After incubation with the appropriate antibiotic, a live cell line designated PU34 was selected for its growth characteristics and induced with IL-1 alpha expressed in *E. coli*. Conditioned medium showed activity in a proliferation assay with IL-6 dependent mouse plasmacytoma cells in the presence of neutralizing antibody to IL-6. A cDNA library was prepared from IL-1-stimulated (2u/ml IL-1 for 24 hours) PU34 cell mRNA according to the expression cloning method previously described in, e.g., G. G. Wong et al, *Science*, 228:810–815 (1985); Y. C. Yang et al, *Cell*, 47:3–10 (1986); and A. E. Namen et al, *Nature*, 333:571–573 (1988).

The library was constructed in an expression vector which permits the expression of cDNA inserts in mammalian cells, e.g. COS-1 cells. Screening of the library was performed by transfecting COS-1 cells with 5 μg of DNA prepared from pools of 200–500 cDNA clones. By assaying the supernatant fluid for activity in the T1165 assay, cDNA clones expressing IL-11 activity were identified.

An isolated clone having T1165 activity was called pPU34-TRA (also called pC1R6) and was sequenced. Table I illustrates the cDNA sequence and the amino acid sequence (single letter code) of both the primate and human clones of the IL-11 polypeptide. The nucleotide sequence from position 1–721 for the primate sequence was obtained from pC1R6. The remainder, from nucleotides 721–1102 was sequenced from a second primate cDNA isolated.by hybridization with pC1R6. A human cDNA encoding the plasmacytoma stimulatory activity of IL-11 was isolated from a cDNA library prepared from the human lung cell line, MRC5 described by Jacobs et al, *Nature*, 227: 43 (1970) by direct hybridization with the insert from pPU34-TRA (pC1R6). The differences found in the human IL-11 nucleotide sequence are indicated in Table I above the primate sequence and the resulting changes in amino acid sequences are indicated below the appropriate amino acid in the primate sequence.

The primate nucleotide sequence comprises 1100 base pairs. The primate sequence contains a 5' non-coding sequence of 72 base pairs. The sequence of Table I also shows a 3' non-coding sequence of 431 bases. The human nucleotide sequence similarly contained a single long reading frame of 597 nucleotides.

Both the primate and the human sequences are characterized by a single long open reading frame predicting an unprocessed 199 amino acid polypeptide which begins at primate nucleotide position 73 in Table I. The first 21 amino acids from positions (1) Met to position (21) Ala in the predicted amino acid sequence of IL-11 from both the primate and human clones contain a stretch of hydrophobic amino acids that resembles a conventional mammalian secretory leader sequence [D. Perlman et al, *J. Mol. Biol.*, 167:391–409 (1983)]. The N-terminal of the mature IL-11 protein (underlined in Table I) and consists of the amino acid sequence PRO-GLY-PRO-PRO-PRO-GLY. The protein is first synthesized as a precursor of 199 amino acids which gets proteolytically cleaved between nucleotides #135–136, to yield a mature 178 amino acid polypeptide beginning with the sequence Pro-Gly at amino acid positions 22–23 and terminating after amino acid position 199 at the TGA termination triplet at nucleotide positions 671–672. The calculated molecular mass of the mature protein correspond well with the apparent molecular weight of a novel protein band revealed by SDS-PAGE (reducing conditions) of supernatant fluid derived from IL-11 cDNA transfected COS-1 cells, that is, approximately 20 kd in both cases.

TABLE I

Primate and Human IL-11 sequence, 5'-3'
Differences between human and primate sequence
are indicated by bases above primate nucleotide sequence
and amino acids below primate amino acid sequence.

```
GGGAAGGTGG AAGGGTTAAA GGCCCCCGGC TCCCTGCCCC                               40

CTGCCCTGGG GAACCCCTGG CCCTGCGGGG AC  ATG  AAC  TGT  GTT                  84
                                     Met  Asn  Cys  Val
                                     1

TGC  CGC  CTG  GTC  CTG  GTC  GTG  CTG  AGC  CTG  TGG  CCA  GAT          123
Cys  Arg  Leu  Val  Leu  Val  Val  Leu  Ser  Leu  Trp  Pro  Asp
5                        10                       15

Signal sequence cleavage site
               C            ↓                          C
ACA  GCT  GTT  GCC  CCT  GGG  CCA  CCA  CCT  GGC  TCC  CCT  CGA          162
Thr  Ala  Val  Ala  Pro  Gly  Pro  Pro  Pro  Gly  Ser  Pro  Arg
               20                 25              Pro       30
                    N terminal mature
                         IL-11

T
GCT  TCC  CCA  GAC  CCT  CGG  GCC  GAG  CTG  GAC  AGC  ACC  GTG          201
Ala  Ser  Pro  Asp  Pro  Arg  Ala  Glu  Leu  Asp  Ser  Thr  Val
Val                      35                      40

C
CTC  CTG  ACC  CGC  TCT  CTC  CTG  GAG  GAC  ACG  CGG  CAG  CTG          240
Leu  Leu  Thr  Arg  Ser  Leu  Leu  Glu  Asp  Thr  Arg  Gln  Leu
          45                  50                      55
                                   Ala

G    GC             G
ACT  ATA  CAG  CTG  AAG  GAC  AAA  TTC  CCA  GCT  GAC  GGG  GAC          279
Thr  Ile  Gln  Leu  Lys  Asp  Lys  Phe  Pro  Ala  Asp  Gly  Asp
Ala  Ala       60   Arg                65

T
CAC  AAC  CTG  GAT  TCC  CTG  CCC  ACC  CTG  GCC  ATG  AGC  GCG          318
His  Asn  Leu  Asp  Ser  Leu  Pro  Thr  Leu  Ala  Met  Ser  Ala
70                       75                       80

A    G
GGG  GCA  CTG  GGA  GCT  CTA  CAG  CTC  CCG  AGT  GTG  CTG  ACA          357
Gly  Ala  Leu  Gly  Ala  Leu  Gln  Leu  Pro  Ser  Val  Leu  Thr
          85                       90        Gly                95

C
AGG  CTG  CGA  GCG  GAC  CTA  CTG  TCC  TAC  CTG  CGG  CAT  GTG          396
Arg  Leu  Arg  Ala  Asp  Leu  Leu  Ser  Tyr  Leu  Arg  His  Val
                    100                      105

C              GGT
CAG  TGG  CTG  CGT  CGG  GCA  ATG  GGC  TCT  TCC  CTG  AAG  ACC          435
Gln  Trp  Leu  Arg  Arg  Ala  Met  Gly  Ser  Ser  Leu  Lys  Thr
     110                      Gly                       120
                              115

C                             G     A
CTG  GAG  CCT  GAG  CTG  GGC  ACC  CTG  CAG  ACC  CGG  CTG  GAC          474
Leu  Glu  Pro  Glu  Leu  Gly  Thr  Leu  Gln  Thr  Arg  Leu  Asp
               125                      130  Ala

CGG  CTG  CTG  CGC  CGG  CTG  CAG  CTC  CTG  ATG  TCC  CGC  CTG          513
Arg  Leu  Leu  Arg  Arg  Leu  Gln  Leu  Leu  Met  Ser  Arg  Leu
135                      140                      145
```

TABLE I-continued

Primate and Human IL-11 sequence, 5'-3'
Differences between human and primate sequence
are indicated by bases above primate nucleotide sequence
and amino acids below primate amino acid sequence.

```
                    CA              G
GCC CTG CCC CAG CTG CCC CCA GAC CCG CCG GCG CCC CCG  552
Ala Leu Pro Gln Leu Pro Pro Asp Pro Pro Ala Pro Pro
            150     Pro     155                 160

G
CTG GCG CCC CCC TCC TCA ACC TGG GGG GGC ATC AGG GCC  591
Leu Ala Pro Pro Ser Ser Thr Trp Gly Gly Ile Arg Ala
                165     Ala         170

GCC CAC GCC ATC CTG GGG GGG CTG CAC CTG ACA CTT GAC  630
Ala His Ala Ile Leu Gly Gly Leu His Leu Thr Leu Asp
    175                 180                 185

A       G
TGG GCC GTG AGG GGG CTA CTG CTG CTG AAG ACT CGG CTG  669
Trp Ala Val Arg Gly Leu Leu Leu Leu Lys Thr Arg Leu
            190                 195             199

TGA CCCGAGGCCC AGAGCCACCA CCGTCCTTCC                 702
End

AAAGCCACAT CTTATTTATT TATTTATTTC GGTACTGGGG          742

GCGAAACAGC CAGGTGATCC CCCTGCCTTT AGCTCCCCCT          782

AGTTAGAGAC AGTCCTTCCG TGAGGCTGGG GGGCATCTGT          822

GCCTTATTTA TACTTATTTA TTTCAGGAGC GGGGGTGGGC          862

TCCTGGGTCC CCGAGGAGGA GGGAGCTGGG GTCCCGGATT          902

CTTGTGTCCA CAGACTTCTG CCCTGGCTCC TCCCCCTCGA          942

GGCCTGGGCA GGAATACATA CTATTTATTT AAGCAATACC          982

TTTTCATGTT GGGGTGGGGA GGGAGGGGAA AGGGAAGCCT         1022

GGGTTTTTGT ACAAAAATGT GAGAAACCTT TGTGAGACGG         1062

AGAACAAGGA ATTAAATGTG TCATACATAA AAAAAAAA          1100
```

The nucleotide sequence of IL-11 cDNA has been compared with the nucleotide sequences recorded in Genbank. No significant similarities in nucleotide sequence were found with the published DNA sequences of other proteins. Only mild homology was found between the leader sequence of IL-11 and those of gamma interferon and IL-6. No significant homology was found between the coding sequence of IL-11 and any other published polypeptide sequence.

Additionally, as described in more detail in Example 11, IL-11 is a synergistic factor for IL-3-dependent proliferation of primitive progenitors. A result of the synergism is the shortening of the $G_o$ period of the stem cells. In at least one culture system, IL-11, like IL-6, acts synergistically with IL-3 in support of megakaryocyte colony formation [S. R. Paul et al, Proc. Natl. Acad. Sci. U.S.A., 87:7512–7516 (1990)]. Thus, it appears that IL-11, as well as G-CSF and IL-6, interacts with early and late hempoietic lineages. However, in constrast to IL-6, which is also such a synergistic factor, IL-11 preferentially stimulates only macrophage proliferation in secondary cultures of pooled blast cells. Thus, IL-11 appears to be distinct from other known lymphokines, factors and proteins. IL-11 is also implicated in playing a role within the lymphoid lineages, resulting in stimulation of multiple arms of the defense system. Thus, IL-11 is expected to be useful in the manipulation of stem cells for both experimental and clinical purposes.

The biological activity of the mammalian IL-11 encoded by this sequence was detected in the functional polypeptides produced by mammalian cells transfected with the cloned sequence under the control of appropriate expression control sequences. The cloned primate sequence in plasmid pPU34-TRA (pC1R6) as reported in Table I was deposited with the American Type Culture Collection, 12301 Parklawn Drive, Rockville, Md. on Nov. 14, 1989 under ATCC No. 68172. The cloned human sequence, illustrated in Table I by the modifications from the primate sequence on both the nucleotide and amino acid levels, was deposited with the American Type Culture Collection, 12301 Parklawn Drive, Rockville, Md. on March 30, 1990 under ATCC No. 68284.

The IL-11 polypeptide is active in the T1165 assay, described below. In initial studies, IL-11 was found to significantly enhance the formation of immunoglobulin-secreting B cells in a standard murine spleen cell plaque formation assay, even at final dilutions as high as 1:500. This system measures the development of B cells in culture that respond to a specific immunogen, 4-hydroxy-3-nitrophenyl-acetyl-modified horse red blood cells (NP-HRBC) in the context of the normal cellular constituents of the spleen. Thy 1 complement-mediated depletion of T cells from the spleen cell cultures resulted in complete abrogation of the response, demonstrating that the increase in NP-responding B cells, even in the presence of the primate IL-11, depends at least in part on the presence of T cells. The activity of IL-11 is therefore not attributable to a direct B cell mitogenic effect because B cell mitogens, such as lipopolysaccharide, stimulate the formation of NP-specific plaque forming cells in the absence of T cells. Thus IL-11 may regulate the proliferation, differentiation and activation of T and B lymphocytes.

Analysis of the effects of the IL-11 in a variety of hematopoietic culture systems revealed striking effects on megakaryocyte development. With murine bone marrow cells as targets, IL-11 had little effect alone, but stimulated by threefold megakaryocyte colony formation supported by IL-3. CFU-Meg formation with IL-3 and IL-11 exceeded that of aplastic canine serum which is used as a positive control.

The IL-11 polypeptides provided herein also include factors encoded by sequences similar to that of recombinant IL-11 in Table I, but into which modifications are naturally provided or deliberately engineered. Thus the present invention also encompasses these novel DNA sequences, free of association with DNA sequences encoding other primate proteins, and coding on expression for IL-11 polypeptides. These DNA sequences include sequences the same or substantially the same as the above-identified DNA sequence and fragments thereof, and those sequences which hybridize under stringent hybridization conditions [see, T. Maniatis et al, *Molecular Cloning* (*A Laboratory Manual*), Cold Spring Harbor Laboratory (1982), pages 387 to 389] to the DNA sequence of Table I. An example of one such stringent hybridization condition is hybridization at 4×SSC at 65° C., followed by a washing in 0.1×SSC at 65° C. for an hour. Alternatively an exemplary stringent hybridization condition is 50% formamide, 4×SSC at 42° C.

DNA sequences which hybridize to the sequences for IL-11 or active fragments thereof under relaxed hybridization conditions and which code on expression for IL-11 peptides having IL-11 biological properties also encode novel IL-11 polypeptides. Examples of such non-stringent hybridization conditions are 4×SSC at 50° C. or hybridization with 30–40% formamide at 42° C. For example, a DNA sequence which shares regions of significant homology with the sequences of IL-11 and encodes a protein having one or more IL-11 biological properties clearly encodes a IL-11 polypeptide even if such a DNA sequence would not stringently hybridize to the IL-11 sequence of Table I or to fragments thereof encoding peptides with IL-11 activity.

Similarly, DNA sequences which code for IL-11 polypeptides but which differ in codon sequence due to the degeneracies of the genetic code are also encompassed by this invention. Allelic variations (naturally-occurring base changes in the species population which may or may not result in an amino acid change) in DNA sequences encoding the IL-11 protein sequences and peptide fragments thereof evidencing IL-11 biological activity are also included in the present invention as well as analogs or derivatives thereof. Other variations in the DNA sequence of IL-11 which are caused by point mutations or by induced modifications to enhance certain characteristics of the IL-11 protein, such as the biological activity, half-life or production of the polypeptides encoded thereby are also encompassed in the invention.

In addition to the use of the cDNA sequence above in recombinant techniques, IL-11 polypeptides of this invention may also be produced by known conventional chemical synthesis. Methods for constructing the polypeptides of the present invention by synthetic means are known to those of skill in the art. The synthetically-constructed IL-11 polypeptide sequences or fragments thereof which duplicate or partially duplicate continuous sequences of the amino acid residues of Table I are also part of this invention. The synthetically-constructed IL-11 polypeptide sequences, by virtue of sharing primary, secondary, or tertiary structural and conformational characteristics with natural IL-11 polypeptides may possess IL-11 biological properties in common therewith. Thus, they may be employed as biologically active or immunological substitutes for natural, purified IL-11 polypeptides in therapeutic and immunological processes.

Modifications in the protein, peptide or DNA sequences of IL-11 or active fragments thereof can be made by one skilled in the art using known techniques. Modifications of interest in the IL-11 sequences may include the replacement, insertion or deletion of one or more selected amino acid residues in the coding sequences. Mutagenic techniques for such replacement, insertion or deletion are well known to one skilled in the art. [See, e.g., U.S. Pat. No. 4,518,584.]

Other specific mutations of the sequences of the IL-11 polypeptide described herein may involve, e.g., the insertion of one or more glycosylation sites. An asparagine-linked glycosylation recognition site can be inserted into the sequence by the deletion, substitution or addition of amino acids into the peptide sequence or nucleotides into the DNA sequence. Such changes may be made at any site of the molecule that is modified by addition of O-linked carbohydrate or at other sites in the molecule. Expression of such altered nucleotide or peptide sequences produces variants which may be glycosylated at those sites and which may have altered or improved pharmacological or biologic properties.

Additional analogs and derivatives of the sequence of IL-11 which would be expected to retain IL-11 activity in whole or in part may also be easily made by one of skill in the art given the disclosures herein. One such modification may be the attachment of polyethylene glycol (PEG) onto existing lysine residues in the IL-11 sequence or the insertion of one or more lysine residues or other amino acid residues that can react with PEG or PEG derivatives into the sequence by conventional techniques to enable the attachment of PEG moieties. Such modifications are believed to be encompassed by this invention.

The present invention also provides a method for producing IL-11 polypeptides or active fragments thereof. One method of the present invention involves introducing the cDNA encoding an IL-11 polypeptide into an expression vector to make an expression system for IL-11. A selected host cell is transformed with the vector and cultured. The method of this present invention therefore comprises culturing a suitable cell or cell line, which has been transformed with a DNA sequence coding on expression for an IL-11 polypeptide or a fragment thereof under the control of known regulatory sequences. The expressed factor is then recovered, isolated and purified from the culture medium (or from the cell, if expressed intracellularly) by appropriate means known to one of skill in the art.

Suitable cells or cell lines for this method may be mammalian cells, such as Chinese hamster ovary cells (CHO) or 3T3 cells. The selection of suitable mammalian host cells and methods for transformation, culture, amplification, screening and product production and purification are known in the art. See, e.g., Gething and Sambrook, *Nature*, 293:620–625 (1981), or alternatively, Kaufman et al, *Mol. Cell. Biol.*, 5(7):1750–1759 (1985) or Howley et al, U.S. Pat. No. 4,419,446. Other suitable mammalian cell lines are the monkey COS-1 cell line and the CV-1 cell line. Further exemplary mammalian host cells include particularly primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, HeLa, mouse L-929 cells, 3T3 lines derived from Swiss, Balb-c or NIH mice, BHK or HaK hamster cell lines.

Similarly useful as host cells suitable for the present invention are bacterial cells. For example, the various strains of *E. coli* (e.g., HB101, and MC1061) are well-known as host cells in the field of biotechnology. Various strains of *B. subtilis*, Pseudomonas, other bacilli and the like may also be employed in this method.

Many strains of yeast cells known to those skilled in the art are also available as host cells for expression of the polypeptides of the present invention. Additionally, where desired, insect cells may be utilized as host cells in the method of the present invention. See, e.g. Miller et al, *Genetic Engineering*, 8:277–298 (Plenum Press 1986) and references cited therein.

The present invention also provides recombinant DNA molecules, or vectors, for use in the method of expression of novel IL-11 polypeptides. These vectors contain the novel isolated DNA sequences which code for IL-11 polypeptides of the invention. Alternatively, vectors incorporating modified sequences as described above are also embodiments of the present invention and useful in the production of IL-11 polypeptides. The vector employed in the method also contains selected regulatory sequences in operative association with the DNA coding sequences of the invention and capable of directing the replication and expression thereof in selected host cells.

The vector used in the examples below is pXM [Y. C. Yang et al, *Cell*, 47:3–10 (1986)]. The mammalian cell expression vectors described herein may be synthesized by techniques well known to those skilled in this art. The components of the vectors, e.g. replicons, selection genes, enhancers, promoters, and the like, may be obtained from natural sources or synthesized by known procedures. See, Kaufman et al, *J. Mol. Biol.*, 159:511–521 (1982); and Kaufman, *Proc. Natl. Acad. Sci. USA*, 82:689–693 (1985). Alternatively, the vector DNA may include all or part of the bovine papilloma virus genome [Lusky et al, *Cell*, 36:391–401 (1984)] and be carried in cell lines such as C127 mouse cells as a stable episomal element. The transformation of these vectors into appropriate host cells can result in expression of the IL-11 polypeptides.

Other appropriate expression vectors of which numerous types are known in the art for mammalian, insect, yeast, fungal and bacterial expression can also be used for this purpose.

IL-11, purified to homogeneity from cell sources or produced recombinantly or synthetically, may be used in a pharmaceutical preparation or formulation to treat immune deficiencies or disorders. IL-11 may also be employed to treat deficiencies in hematopoietic progenitor or stem cells, or disorders relating thereto. IL-11 compositions may be employed in methods for treating cancer and other pathological states resulting from disease, exposure to radiation or drugs, and including for example, leukopenia, bacterial and viral infections, anemia, B cell or T cell deficiencies, including immune cell or hematopoietic cell deficiency following a bone marrow transplantation. IL-11 may also be used to potentiate the immune response to a variety of vaccines creating longer lasting and more effective immunity. As mentioned previously, IL-11 compositions may be employed to stimulate development of B cells, and megakaryocytes. Therapeutic treatment of such disease states with these IL-11 polypeptide compositions may avoid undesirable side effects caused by treatment with presently available drugs.

The polypeptides of the present invention may also be employed, alone or in combination with other cytokines, hematopoietins, interleukins, growth factors or antibodies in the treatment of the above-identified conditions.

The present invention also provides methods and therapeutic compositions for treating the conditions referred to above. Such compositions comprise a therapeutically effective amount of an IL-11 polypeptide of the present invention in admixture with a pharmaceutically acceptable carrier. This composition can be systematically administered parenterally. Alternatively, the composition may be administered intravenously. If desirable, the composition may be administered subcutaneously or topically, e.g., at the site of a wound. When systematically administered, the therapeutic composition for use in this invention is in the form of a pyrogen-free, parenterally acceptable aqueous solution. The preparation of such a pharmaceutically acceptable protein solution, having due regard to pH, isotonicity, stability and the like, is within the skill of the art.

The dosage regimen involved in a method for treating the above-described conditions will be determined by the attending physician considering various factors which modify the action of drugs, e.g. the condition, body weight, sex and diet of the patient, the severity of any infection, time of administration and other clinical factors. Generally, the daily regimen should be in the range of 1–1000 micrograms of polypeptide or 50 to 5000 units (i.e., a unit being the concentration of polypeptide which leads to half maximal stimulation in the T1165 assay) of polypeptide per kilogram of body weight.

The therapeutic method and compositions of the present invention may also include co-administration with other human factors. Exemplary cytokines or hematopoietins for such use include the known factors IL-1 through IL-9, GM-CSF, G-CSF, M-CSF, MIF, Meg-CSF, the interferons, TNF and erythropoietin. Particularly desirable candidates for participation in IL-11 therapy may include IL-3 and IL-6. Growth factors like B cell growth factor, B cell differentiation factor, or eosinophil differentiation factors may also prove useful in co-administration with IL-11. The dosage recited above would be adjusted to compensate for such additional components in the therapeutic composition. Progress of the treated patient can be monitored by conventional methods.

Other uses for these novel polypeptides are in the development of antibodies generated by standard methods for in vivo or in vitro diagnostic or therapeutic use. Such antibodies may include both monoclonal and polyclonal antibodies, as well as chimeric antibodies or "recombinant" antibodies generated by known techniques. Also provided by this invention are the cell lines generated by presenting IL-11 or a fragment thereof as an antigen to a selected mammal, followed by fusing cells of the animal with certain cancer cells to create immortalized cell lines by known techniques. The methods employed to generate such cell lines and antibodies directed against all or portions of a mammalian IL-11 polypeptide of the present invention are also encompassed by this invention.

The antibodies of the present invention may be utilized for in vivo and in vitro diagnostic purposes, such as by associating the antibodies with detectable labels or label systems. Alternatively these antibodies may be employed for in vivo and in vitro therapeutic purposes, such as by association with certain toxic or therapeutic compounds or moieties known to those of skill in this art.

The following examples illustratively describe the cloning, expression and production of mammalian IL-11 and other methods and products of the present invention. These examples are for illustration and do not limit the scope of the present invention.

EXAMPLE 1

Isolation of mRNA and Construction of cDNA Library

A primate cell line, pU34, was developed and was found to elaborate significant activity in the T1165 assay of Example 7 in the presence of neutralizing antibody to IL-6. The PU-34 stromal cell line was derived from a long term primate marrow culture by immortalization with a defective amphotropic transforming retroviral vector. The U19 retrovirus plasmid was constructed as previously reported [P. S. Jat et al, *J. of Virol.*, 59:746–750 (1986)] and contains SV40 large T antigen sequence and the neo-phosphotransferase sequence encoding G418-resistance expressed off the Moloney murine leukemia virus long terminal repeat. An amphotropic producer clone was generated by infection of the packaging cell line ψAM [R. Cone et al, *Proc. Natl. Acad. Sci., USA*, 81:6349–6353 (1984)] with ecotropic viral harvest from ψ2U19–5 [P. S. Jat, cited above] followed by selection in 0.75 mg/ml G418.

One clone ψAMU19-BL produces recombinant SV40 virus at a titer of 5×10³ G418-resistant CFU/ml when assayed on NIH/3T3 cells. Long term marrow cultures (LTMC) were established using standard methods and maintained in Iscove's Modified Dulbecco's Medium (IMDM) supplemented with 10% fetal calf serum, 10% horse serum, 100 units/ml penicillin and 100 μg/ml streptomycin (Sigma Chemical Co., St. Louis, Mo.) complete long term culture medium.

The LTMC adherent layer was infected 7 and 10 days after establishment with 2 ml of ψAMU19-BL viral stock in the presence of 8 μg/ml of polybrene (Aldrich Chemical Co., Inc., Milwaukee, Wis.) for 2.5 hours at 33° C. Beginning three days after infection, the cultures were selected in 0.5 mg/ml G418. Fourteen days after infection G418-resistant colonies were picked and expanded in multiwell plates (Corning Glassware, Corning, N.Y.).

The conditioned medium from one cell line, designated PU-34, was extensively analyzed based on its ability to support progenitor cells in long term cultures. This cell line demonstrated the capacity to maintain multipotent human and primate progenitor cells for up to three weeks in culture. In addition to known growth factor activities including IL-6, IL-7, GM-CSF, M-CSF, G-CSF and LIF/HILDA, the IL1-α-stimulated PU-34 conditioned medium proved capable of stimulating the proliferation of the T1165 murine plasmacytoma cell line, which is normally responsive to IL-6 [R. P. Nordan et al, cited above], even in the presence of a neutralizing antiserum against human IL-6. This bioassay was used during expression cloning of a cDNA library generated from PU-34. The bioassay is described in detail in Example 7 below.

The cDNA library from PU-34 cells was prepared as follows: PU-34 cells were stimulated for 24 hours with IL1-α at a concentration of 2 units/ml. Poly adenylated RNA (poly A+ RNA) was prepared from these cells by standard methods. Total RNA was extracted according to the method of Chirgwin et al, *Biochemistry*, 18:5294–5299 (1979) from the stimulated pU34 cells. mRNA was prepared by oligo (dT)-cellulose chromatography [H. Aviv et al, *Proc. Natl. Acad. Sci. USA*, 69:1408–1412 (1972)].

Five micrograms of mRNA was used to synthesize double-stranded cDNA as described by Wong et al, cited above, with DNA polymerase I and RNAse H in the second strand reaction [T. Maniatis et al, cited above]. The Cos-1cell expression vector pXM [Y. C. Yang et al, *Cell 47: 3–10* (1986)] was linearized at the unique Xho I site and ligated to equimolar amounts of semi-Xho I adapted cDNA. The ligation reaction was used to transform competent *E. coli* (strain HB101) [Y. C. Yang et al, cited above] to generate a library of approximately 500,000 ampicillin-resistant colonies.

EXAMPLE 2

DNA Preparation and COS-1 Cell Transfection

The expression cloning system previously described by G. G. Wong et al, cited above, was employed to isolate a cDNA encoding the IL-11 activity as follows.

Bacterial colonies were replicated onto nitrocellulose filters. Colonies from each filter were scraped into L-broth and plasmid DNA was isolated by previously described methods [J. A. Meyers et al, *J. Bacteriol.*, 127:1529–1536 (1976)]. Each primary DNA sample was prepared from a pool of 200–500 colonies.

Five micrograms of each plasmid DNA was used to transfect Cos-1 cells by the diethylaminoethyl-dextran (DEAE) protocol with the addition of 0.1 mM chloroquine [L. M. Sompayrac et al, *Proc. Natl. Acad. Sci. USA*, 78:7575–7578 (1981) and H. Luthman et al, *Nucl. Acids Res.*, 11:1295–1308 (1983)]; Y. C. Yang et al, cited above. Culture supernatant from transfected Cos-1 cells was harvested 72 hours after transfection and assayed for T1165 stimulatory activity (see Example 7).

Of the 317 pools screened, plasmid DNA from the two positive pools which contained detectable levels of IL-6 (as determined by neutralization with anti-IL-6 antibody) and residual activity in the T1165 assay in the presence of anti-IL-6 antibody, were re-transfected into COS-1 cells and transfected supernatants were re-screened for activity in the T1165 assay. One pool with such activity was selected and subdivided to contain fewer number of clones. A pool from this group was selected which demonstrated higher activity in the assay than the total collection of pools. Individul colonies were picked from this pool. Their DNAs were prepared, transfected, and the transfected supernatants were examined for activity in the T1165 assay. Two positive clones were identified, one expressing IL-6 activity and the other expressing activity unneutralized by anti-IL-6 antibodies. This latter pool was subdivided and the transfection process repeated until a single positive plasmid, called alternatively pC1R6 or pPU34-TRA, was obtained which encoded the novel T1165 proliferation activity. This clone was re-examined in the assay of Example 7.

The activity from the conditioned medium from pC1R6-transfected Cos-1 cells was also compared with other cytokines, e.g., murine and human IL-6 and murine GM-CSF. The conditioned medium stimulated measurable incorporation of $^3$H-thymidine by T1165 cells, even at final dilutions up to 1:1000. At optimal concentrations the novel cytokine supported incorporation that was more than 100 fold above background levels.

The insert of this cDNA was sequenced by the dideoxy chain termination method on super-coiled templates with synthetic oligonucleotide primers [F. Sanger et al, *Proc. Natl. Acad. Sci. USA*, 74:5463–5467 (1977)]. The nucleotide sequence of the pC1R6 cDNA shown in Table I contains a single long open reading frame of 597 nucleotides encoding a predicted 199 amino acid polypeptide. Located immediately adjacent to the putative initiation codon is a stretch of 17–20 hydrophobic amino acids that resembles a conventional protein secretory leader sequence.

Although the initial cDNA clone, pC1R6, proved to be incomplete, analysis of additional cDNAs revealed that this transcript contains approximately 420 base pairs of 3' noncoding sequence with multiple copies of the RNA instability sequence, ATTTA, believed to be an important regulatory element for cytokine gene expression [G. Shaw et al, *Cell*, 46:659–667 (1986)].

EXAMPLE 3

Protein Analysis

The polypeptide encoded by the cDNA of pPU34-TRA was identified using pulse-labeling experiments. Forty-eight hours after induction with chloroquine, culture supernatant from COS-1 cells transfected with recombinant DNA of IL-11 clones was removed and cells were pulse-labeled with 0.5 mCi [$^{35}$S] methionine in 1.0 ml of DMEM for four hours at 37° C. Ten microliter samples of the radiolabelled supernatant were collected and subjected to a 15% SDS-PAGE with the Laemmli buffer system on a 12% gel [U. K. Laemmli, *Nature*, 227:680–685 (1970)]. After electrophoresis, the gel was immersed in a fluorography enhancing solution (Enhance; New England Nuclear, Boston, Mass.), dried, and exposed to X-ray film.

SDS-polyacrylamide gel electrophoresis (SDS-PAGE) analysis of conditioned medium from $^{35}$S-methionine labelled pC1R6-transfected cos-1 cells revealed the presence of a prominent 20 kD species that was not present in mock-transfected controls consistent with the molecular mass expected for an approximately 180 amino acid secreted protein.

This size estimate as well as the lack of heterogeneity of the expressed protein are in accordance with the absence of the consensus sequence (Asn-X-Thr/Ser) [R. J. Winzler in "Hormonal Proteins and Peptides", ed. Li, C. H. (Academic Press, New York), pp. 1 (1973)] for the addition of asparagine-linked carbohydrate. The predicted amino acid sequence of the mature protein includes no cysteine residues, a feature not found with any other cytokine gene.

EXAMPLE 4

Human Cell Lines Expressing IL-11

Two human cell lines have been identified as sources of at least one species of IL-11. Specifically, the human lung fibroblast cell line, MRC-5, available from the American Type Culture Collection under Accession number ATCC CCL 171, when induced with one unit/ml of recombinant human IL-1-alpha (Genetics Institute, Inc.) and $10^{-7}$M phorbol 12–13 dibutyrate (Sigma), has been tested on the T1165 assay. The induced conditioned medium was observed to exhibit greater cpm on the assay than does IL-6 at saturation levels, i.e., similar activity to that exhibited by the induced conditioned medium of PU34. It has been noted that the presence of IL-11 will enhance a low IL-6 signal. In addition, as detailed below, Northern blot of this cell line reveals the presence of message for IL-11.

Additionally the human trophoblastic cell line, TPA30-1, available from the ATCC under Accession Number CRL 1583 also reveals uninduced the presence of IL-11 message in Northern blots.

Other human sources for IL-11 may also be available and easily identified given the teachings of the present invention.

EXAMPLE 5

RNA Analysis

A. PU34

Five micrograms of total cellular RNA from bacterial IL-1-alpha induced PU34 cells was electrophoresed through 1.2% agarose gel containing 2.2M formaldehyde [H. Lehrach et al, *Biochemistry*, 16:4743 (1977)]. The formaldehyde-denatured RNA was transferred to nylon filter (Zetabind; Cuno, Meriden, Conn.) as described [E. M. Southern, *J. Mol. Biol.*, 98:503–517 (1975)] and probed with $^{32}$P-labelled cDNA probes.

A cDNA probe was made by cleaving cDNA inserts from the vector with Xho I restriction enzyme and labelled the inserts with $^{32}$P-dCTP using random oligonucleotides as primers in the presence of the large fragment of DNA polymerase I [A. P. Feinberg et al, *Analy. Biochemistry*, 132:6–13 (1983)]. The nylon filter was prehybridized for 4 hours at 65° C., hybridized with $^{32}$P-dCTP labelled cDNA probe in hybridization solution consisted of 4×SSC, 0.5% SDS 5× Denhardt's solution and 100 ug/ml denatured salmon sperm DNA for 16 hours at 65° C. Other probes used included human (rh) IL-1α, rhIL-2, rhIL-3, rhIL-4, rhIL-5, rhIL-6, rhIL-7, rhIL-9, rhGM-CSF, rhM-CSF, LIF/HILDA and primate IL-11.

After hybridization, the filter was washed two times with 2×SSC/0.1% SDS for 30 minutes at 65° C., then with 0.2×SSC/0.1% SDS for 30 minutes at 65° C. The filter was then dried and applied to X-ray film in the presence of a calcium tungstate intensifying screen at −70° C.

This Northern blot analysis revealed that PU34 mRNA contained two species of IL-11 transcripts, with message sizes of approximately 2.5 kb and approximately 1.5 kb which hybridize with the pCIR6 probe. The size of the cDNA sequence of Table I above correlates well with the smaller message. This difference results from alternative splicing to yield additional 3' noncoding sequences in the larger transcript as demonstrated by isolation and analysis of additional cDNA clones. The presence of the two transcripts by PU34 cells appears to be IL-1α regulated since neither transcript was evident in the absence of IL-1α induction.

Neither transcript was identified by RNA blot analysis in preparations of mRNA from the human T cell lines C10-MJ2 [Leary et al, *Blood*, 69:953 (1987)], C5-MJ2 [Arya et al, *Science*, 223:1086 (1984)], and Mo [Golde et al, *Proc. Natl. Acad. Sci., USA*, 77:593 (1980)] from lectin-stimulated human peripheral blood lymphocytes or from human placental. Thus, it appears the only identified source of IL-11 is mesenchymal-derived adherent cells.

B. MRC-5

The human fetal lung fibroblast cell line (MRC-5) as described by Jacobs et al, *Nature*, 227:43 (1970) was found to express both transcripts following stimulation with 50 ng/ml phorbal myristate acetate (PMA) and 1 unit/ml IL-1α.

As described above for PU34 RNA, two species of transcripts were identified with identical message sizes of approximately 2.5 kb and approximately 1.5 kb in this cell line. Analysis of the human cDNA sequence isolated from the MRC-5 cell line revealed that the primate and human coding regions share approximately 95% identity at the nucleotide level.

C. TPA30-1

When the same procedures were performed on the human SV40-transformed trophoblastic cell line, TPA30-1, using the same probe, only the larger approximately 2.3 kb IL-11 message, was identified.

EXAMPLE 6

DNA Sequence Analysis

The nucleotide sequence of the cDNA clone of pPU34-TRA was determined as described [G. G. Wong et al and Y. C. Yang et al, cited above] by generating ordered sets of overlapping fragments via Bal 31 nuclease digestion and subcloning into M13 vector [M. Poncz et al, *Proc. Natl. Acad. Sci. USA*, 79:4298–4302 (1982); and J. Messing et al, *Gene*, 19:269–276 (1982)]. Single-stranded DNA was prepared, and the nucleotide sequence was determined by the dideoxynucleotide chain-termination procedure. [F. Sanger et al, *Proc. Natl. Acad. Sci. USA*, 74:5463–5467 (1977)]. This nucleotide sequence appears in Table I above.

EXAMPLE 7

Biological Activity in Assays.

A. T1165 Proliferation Assay

T1165 IL-6 dependent murine plasmacytoma cells [R. P. Nordan et al, *Science*, 233:566 (1986); and obtained from Dr. Nordan, National Institutes of Health] are routinely grown in RPMI supplemented with 10% heat-inactivated fetal calf serum, 2 mM glutamine, 100 u/ml penicillin, 100 μg/ml streptomycin (all Gibco, Grand Island, N.Y.), $5 \times 10^{-5}$ M beta mercaptoethanol (Sigma Chemical Co., St. Louis, Mo.), and supplemented with 10–20 U/ml recombinant human IL-6 produced in CHO cells (Genetics Institute, Inc.). Two to four days following passage, the cells are removed from culture, washed to remove residual IL-6 and resuspended at a concentration of $7.5 \times 10^4$ to $1 \times 10^5$ cells/ml.

Serial dilutions of the sample to be assayed (either PU34 conditioned medium or pC1R6-transfected Cos cell conditioned medium) are made in duplicate in 100 μl of culture medium without IL-6 on 96-well microtiter plates. 100 μl of the above cell suspension is then added to each well and the plates are incubated at 37° C. for 2–3 days; 0.5 μCi of $^3$H-thymidine [DuPont, Wilmington, Del.] is added per well for the final six hours of the assay. Cells are harvested onto GFC type C filter paper (LKB), washed with water and ethanol and dried. The filters are then immersed in scintillation fluid and counted on an LKB flatbed scintillation counter. Proliferation is measured by $^3$H-thymidine uptake.

Induced conditioned medium from the PU34 cells caused greater proliferation of the T1165 cells than saturating levels of IL-6, suggesting the presence of another factor. When assayed in the presence of antibody to human IL-6, a low but significant activity remained in the conditioned medium. Fractionated samples of conditioned medium from IL-1-induced PU34 containing very low levels of IL-6 were also assayed with and without antibody to human IL-6 and the results suggested the presence of a factor that was proliferative to a low degree by itself and capable of synergizing with low levels of IL-6.

COS cell supernatants from transfection of the pU34 library were also assayed for activity, alone and in the presence of a cocktail of antibody to human IL-6 plus suboptimal levels of murine IL-6. The antibody is capable of neutralizing primate IL-6 produced by the PU34 cells, but not able to neutralize murine IL-6. Therefore, a synergizing factor could be screened for without interference from the PU34 IL-6 present in the library.

The mature IL-11 protein of Table I is characterized by a half-maximal activity of 100 dilution units per ml in this assay.

B. B Cell Plaque Forming Assay

A B Cell plaque forming assay was performed on COS cell expressing IL-11 according to the procedures described in R. M. O'Hara et al, *J. Immunol.*, 141:2935–2942 (1988). The murine plaque forming assay was performed by incubating $7.5 \times 10^6$ spleen cells from naive C57B1/6 mice with $3 \times 10^6$ 4-hydroxy-3-nitrophenyl-acetyl-modified horse red blood cells (NP-HRBC) in 0.75 Mishell-Dutton media [R. I. Mishell et al, *J. Exp. Med.*, 126:423–442 (1967)] supplemented with 5% fetal calf serum with or without test samples (COS cell conditioned media containing IL-11) for 5 days. NP-coupled horse red blood cells (H-RBC) or sheep red blood cells (S-RBC) were prepared by reaction of 10 mg NP-O-Succinimide (Cambridge Biochemical, Inc., Cambridge, England) in dimethyl formamide (Sigma Chemical Co., St. Louis, Mo.) with 1 ml packed H-RBC or S-RBC (Colorado Serum Co., Denver, Colo.) as has been described previously [P. B. Hausman et al, *J. of Immunol.*, 134:1388–1396 (1985)].

These cultures were fed daily by addition of 0.1 ml supplemental medium containing 5% fetal calf serum without test samples (the conditioned media). NP-responsive B-cells were identified at the end of the culture period using the NP-coupled-sheep RBC plaque assay as described by Dresser et al in "Handbook in Experimental Immunology" (D. M. Weir, Blackwell, Oxford), p. 271 (1973) with the percent response calculated by comparing the numbers of plaques obtained from cultures supported with the conditioned medium containing IL-11 with those cultures supplemented with medium alone. In a typical experiment, background responses in the absence of exogenous factors yielded 6000 NP-specific plaque forming cells per $7.5 \times 10^6$ cells plated.

The results of such as assay can be seen in FIG. 1. The percent of control response is the increase in the development of NP-responsive B cells in 5 day cultures of naive spleen cells stimulated with NP-HRBC supported by the indicated dilution of pC1R6-transfected cos-1 cell conditioned medium compared to control cultures supplemented with medium alone. COS-produced mammalian IL-11 produces a 2 and one-half to 3-fold increase in plaque forming units/culture in this assay, indicating the IL-11 plays either a direct role in B cell stimulation and differentiation, or an indirect role in stimulating T cells to secrete other cytokines which influence the B cell response.

C. Murine Fibrin Clot Assay

COS cell produced mammalian IL-11 was also examined for activity in the megakaryocyte colony formation assay performed substantially as described in S. Kuriya et al, *Exp. Hematol.*, 15:896–901 (1987) and modified by the addition of 2% calf serum. Briefly described, the murine colony forming unit megakaryocyte (CFU-Meg) assay was performed by plating $2.5 \times 10^5$ murine bone marrow cells in 0.4 ml of IMDM supplemented with 20% fetal calf serum in 6 well dishes. Clot formation was initiated by addition of 0.25 mg fibrinogen and 0.25 units thrombin (Sigma Chemical Co., St. Louis, Mo.) at 37° C. Test samples at various dilutions were added to the fibrin clot and cultures subsequently incubated for 6 days at 37° C. The clots were fixed with 2.5% glutaraldehyde and stained with 0.5 mg/ml acetylthiocholine iodide as described in S. Kuriya et al, cited above and A. Nakeff et al, *Proc. Soc. ExP. Biol. Med.*, 151:587–590 (1976). Positive colonies (containing only megakaryocytes) were enumerated under direct microscopy. Colony numbers were evaluated in duplicate.

Figure 2:
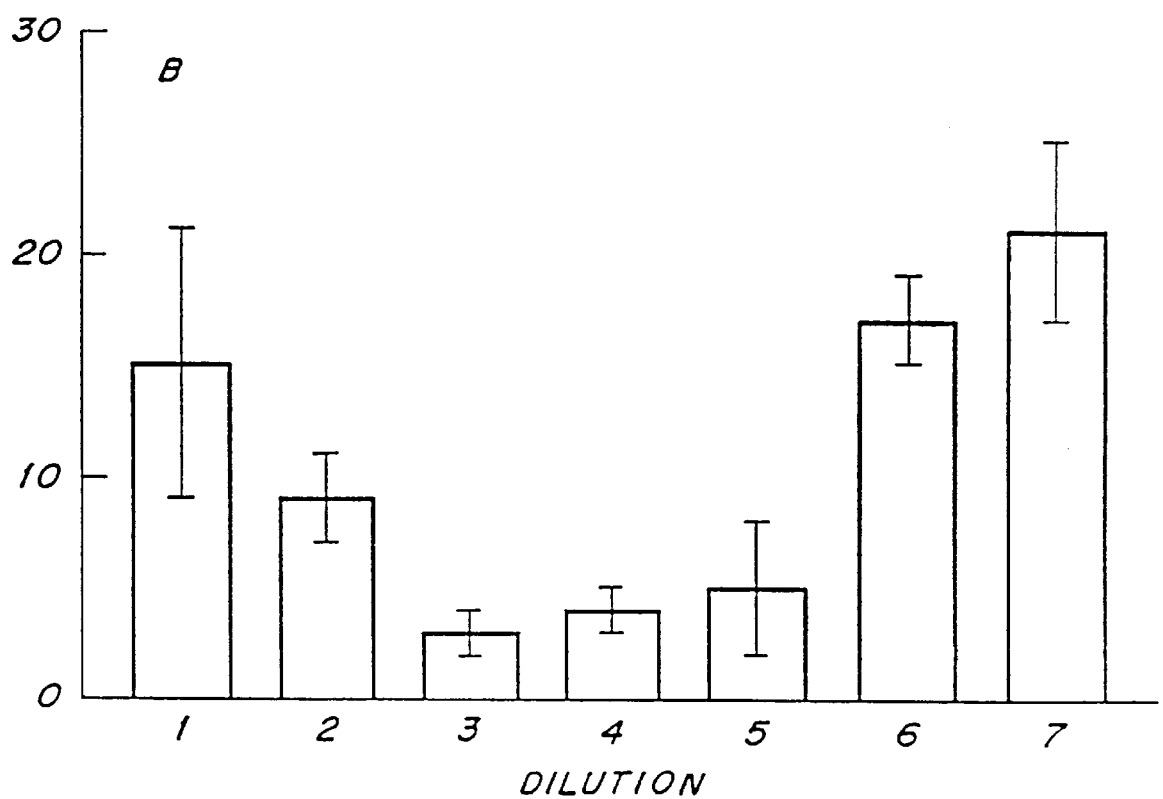
FIG. 2 graphically depicts the enhancement of the development of IL-3-dependent murine megakaryocyte colonies by pC1R6-transfected cos-1 cell conditioned medium in the murine fibrin clot assay.

FIG. 2 illustrates the results. The colony number represents the total number of megakaryocyte colonies (acetylcholinesterase positive cells) in 6 day cultures of mouse bone marrow cells supported by: (1) a 1:10 dilution of canine aplastic anemia serum; (2) 150 units/ml murine IL-3; (3) no stimulus; and dilutions of (4) 1:10 or (5) 1:50 pC1R6-transfected-cos-1 cell conditioned medium alone or dilutions of (6) 1:10 or (7) 1:50 of pC1R6-transfected-cos-1 cell conditioned medium supplemented with 150 units/ml murine IL-3.

When IL-11 was tested in this assay alone, little response was detected. However, when IL-11 was tested in this assay in the presence of recombinant murine IL-3, the assay results demonstrated that the combination of IL-11 and IL-3 stimulated the production and maturation of megakaryocyte cells in this assay to a significant degree. This assay demonstrated that mammalian IL-11 has a synergistic effect with IL-3 in the stimulation of megakaryocyte development.

EXAMPLE 8

Obtaining Human IL-11

To obtain the cloned sequence for human IL-11, the PU34 IL-11 cDNA which hybridized to the human IL-11 mRNA in Example 5 above, was employed to screen a cDNA library prepared from the human lung fibroblast cell line, MRC-5, described above. Recombinants from this library were plated and duplicate nitrocellulose replicase made of the plates. These replicase were hybridized overnight at 65° C. in standard hybridization solution (4×SSC) with the mammalian IL-11 cDNA labelled with $^{32}$P-dCTP using the random priming labelling technique [A. P. Feinberg, cited above]. The filters were then washed in 0.2×SSC at the same temperature until the background radioactivity was lowered to an acceptable level to permit detection of specifically hybridizing sequences. Colonies found to hybridize to the mammalian IL-11 probe on the duplicate filters were picked and used to prepare plasmid DNA.

The full sequence for human IL-11 was determined according to methods analogous to those described above for the isolation of mammalian IL-11 from the PU34 cell line. The human sequence is shown also in Table I. Where the human sequence nucleotides differed from the primate sequence, the human nucleotide is provided above the primate nucleotide sequence in Table I.

Alternatively, oligonucleotides may be constructed from the sequence of Table I with appropriate restriction sites for subcloning purposes, and the Polymerase Chain Reaction employed to generate the human DNA sequence for IL-11. For example, the following oligonucleotides are synthesized:

5' oligonucleotide: 5' ATGGATCCACATGAACTGT-GTTTGCCG 3'

3' oligonucleotide: 5' TCAAGCTTTCACAGC-CGAGTCTTCAGC 3'.

These oligonucleotides are then employed in the Polymerase Chain Reaction in the cDNA library of MRC-5 or TPA30-1, to obtain the DNA sequence for human IL-11 therefrom. The PCR technique is performed according to procedures now standard in the art. The PCR product obtained is then subcloned into an appropriately-digested pXM, or other, expression vector. For the above oligonucleotides, the pXM vector would be digested with BamHI and HindIII for the subcloning.

Still a third method to obtain the sequence of human IL-11 involves screening a human genomic library using the sequence of Table I as a probe.

EXAMPLE 9

Expression of Recombinant IL-11

To produce recombinant mammalian IL-11 including the human factor, the cDNA encoding it is transferred into an appropriate expression vector of which numerous types are known in the art for mammalian, insect, yeast, fungal and bacterial expression by standard molecular biology techniques. See, e.g., Y. C. Yang et al., *Cell*, 47:3–10 (1986).

As described previously for mammalian IL-11, the cDNA for human IL-11 is synthesized using standard techniques and cloned into the expression vector, pXM (Yang et al., cited above). This vector permits the expression of cDNA inserts in mammalian cells, e.g., COS-1 cells. pXM contains the SV40 enhancer, major adenovirus late promoter, tripartite leader sequence, and small hybrid intervening sequence, the DHFR coding sequence, SV40 late message poly A addition site and adenovirus VaI gene. This vector may be linearized with the endonuclease enzyme XhoI and ligated to equimolar amounts of IL-11 cDNA which has been previously modified by the addition of synthetic oligonucleotides that generate complementary XhoI cohesive ends. Such oligonucleotides are commercially available [Collaborative Research, Lexington, Mass.].

Another vector which has been shown to express cytokines well in CHO cells is pEMC2B1. This vector may be derived from pMT2pc which has been deposited with the American Type Culture Collection (ATCC), Rockville, Md. (USA) under Accession Number ATCC 40348. The DNA is linearized by digestion of the plasmid with PstI. The DNA is then blunted using $T_4$ DNA polymerase. An oligonucleotide 5' TGCAGGCGAGCCTGAATTCCTCGA 3' is then ligated into the DNA, recreating the PstI site at the 5' end and adding an EcoRI site and XhoI site before the ATG of the DHFR cDNA. This plasmid is called pMT21. pMT21 is cut with EcoRI and XhoI which cleaves the plasmid at two adjacent cloning sites. An EMCV fragment of 508 base pairs was cut from pMT$_2$ECAT$_1$ [S. K. Jong et al., *J. Virol.*, 63:1651–1660 (1989)] with the restriction enzymes EcoRI and TaqαI. A pair of oligonucleotides 68 nucleotides in length were synthesized to duplicate the EMCV sequence up to the ATG. The ATG was changed to an ATT, and a C is added, creating a XhoI site at the 3' end. A TaqαI site is situated at the 5' end. The sequences of the oligonucleotides were:

5'  CGAGGTTAAAAAACGTCTAGGC-
CCCCCGAACCACGGGGACGTGGTTTTCCTTT
GAAAAACACGATTGC 3' and its complementary strand.

Ligation of the pMT21 EcoRI-to-XhoI fragment to the EMCV EcoRI-to-TaqαI fragment and to the TaqαI/XhoI oligonucleotides produced the vector pEMC2B1. This vector contains the SV40 origin of replication and enhancer, the adenovirus major late promoter, a cDNA copy of the majority of the adenovirus tripartite leader sequence, a small hybrid intervening sequence, an SV40 polyadenylation signal and the adenovirus VA I gene, DHFR and β-lactamase markers and an EMC sequence, in appropriate relationships to direct the high level expression of the desired cDNA in mammalian cells. The EMC2B1 vector is linearized with the endonuclease enzyme EcoRI and subsequently ligated in equimolar amount separately to the cDNA encoding IL-11 that was previously modified by addition of synthetic oligonucleotides that generate EcoRI complementary ends to generate constructs for expression.

The desired vector containing IL-11 is then introduced into appropriate host cells by conventional genetic engineering techniques. The transformed cells are cultured and the expressed IL-11 is recovered and purified from the culture medium using standard techniques.

A. Mammalian Cell Expression

To obtain expression of the IL-11 polypeptide in mammalian host cells, the pXM vector containing the IL-11 DNA sequence is transfected onto COS cells as described in Example 2. The conditioned medium from the transfected COS cells contains IL-11 biological activity as measured in the T1165 assay. Similarly the pEMC-2B1 construct containing the cDNA for IL-11 is transfected into CHO cells.

One skilled in the art can also construct other mammalian expression vectors comparable to the pXM/IL-11 vector by, e.g., inserting the DNA sequence of IL-11 from the respective plasmids with XhoI and employing well-known recombinant genetic engineering techniques and other known vectors, such as pJL3 and pJL4 [Gough et al., *EMBO J.*, 4:645–653 (1985)] and pMT2 (starting with pMT2-VWF, ATCC #67122; see PCT application PCT/US87/00033).

The transformation of these vectors into appropriate host cells can result in expression of the IL-11 polypeptides. Mammalian host cells other than COS cells may also be employed in IL-11 expression. For example, preferably for stable integration of the vector DNA, and for subsequent amplification of the integrated vector DNA, both by conventional methods, CHO cells may be employed as a mammalian host cell of choice.

Once the vectors and host cells are selected and transformed, stable transformants are screened for expression of the IL-11 by standard immunological or enzymatic assays. The presence of the DNA or mRNA encoding the IL-11 polypeptides may be detected by standard procedures such as Southern or Northern blotting. Transient expression of the DNA encoding the polypeptides during the several days after introduction of the expression vector DNA into suitable host cells is measured without selection by activity or immunologic assay, e.g., the T1165 assay, of the proteins in the culture medium.

B. Bacterial Expression Systems

Similarly, one skilled in the art could manipulate the sequence of IL-11 by eliminating any mammalian regulatory sequences flanking the coding sequences and inserting bacterial sequences to create bacterial vectors for intracellular or extracellular expression of the IL-11 polypeptides of the invention by bacterial cells.

The DNA encoding the factor may be further modified to contain different codons for bacterial expression as is known in the art. Preferably the mature IL-11 sequence (the nucleotide encoding amino acids 21 to 199 in Table I) is operatively linked inframe to a nucleotide sequence encoding a secretory leader polypeptide permitting bacterial expression, secretion and processing of the mature variant protein, also as is known in the art. The compounds expressed in bacterial host cells may then be recovered, purified, and/or characterized with respect to physiochemical, biochemical and/or clinical parameters, all by known methods.

Alternatively, the IL-11 may be expressed as a cytoplasmic protein in *E. coli*. In this case, the molecule would most likely have to be refolded after complete denaturation with guanidine hydrochloride, a process also known in the art. The presently preferred method for expression of IL-11 in *E. coli*, involves removing the first 31 codons of the human IL-11 sequence. The following sequence is then attached at codon 32 of the mature human IL-11 sequence:

ATG CCA GGT CCA CCA CCA GGT CCA CCT CGA GTT
1               5                           10

C. Insect or Yeast Cell Expression

Similar manipulations can be performed for the construction of an insect vector [See, e.g., procedures described in published European patent application 155,476] for expression in insect cells. A yeast vector could also be constructed employing yeast regulatory sequences for intracellular or extracellular expression of the proteins of the present invention by yeast cells. [See, e.g., procedures described in published PCT application WO 86/00639 and European patent application EP 123,289.]

EXAMPLE 10

Construction of CHO Cell Lines Expressing High Levels of IL-11

One method for producing high levels of the IL-11 polypeptides of the invention from mammalian cells involves the construction of cells containing multiple copies of the heterologous IL-11 gene. The heterologous gene can be linked to an amplifiable marker, e.g., the dihydrofolate reductase (DHFR) gene for which cells containing increased gene copies can be selected for propagation in increasing concentrations of methotrexate (MTX) according to the procedures of Kaufman & Sharp, *J. Mol. Biol.*, (1982) supra. This approach can be employed with a number of different cell types. Alternatively, the IL-11 cDNA and drug resistance selection gene (e.g., DHFR) may be introduced into the same vector. A preferred vector for this approach is pEMC2B1.

For example, the pXM vector containing a IL-11 gene in operative association with other plasmid sequences enabling expression thereof and the DHFR expression plasmid pAdA26SV(A)3 (Kaufman & Sharp, *Mol. Cell Biol.*, 3(9):1598–1608 (1983) can be co-introduced into DHFR-deficient CHO cells, DUKX-BII, by calcium phosphate coprecipitation and transfection.

Alternatively, the pEMC-2B1 vector containing the IL-11 gene in operative association with other plasmid sequences enabling expression thereof is introduced into DHFR-deficient CHO cells, DUKX-BII, by protoplast fusion and transfection. The IL-11 gene and DHFR marker gene are both efficiently expressed when IL-11 is introduced into pEMC2B1. The IL-11 gene may be introduced into pMT2 as previously mentioned and the resultant vector used in place of pXM/IL-11 and pAdA26SV (A) 3.

DHFR expressing transformants are selected for growth in alpha media with dialyzed fetal calf serum. Transformants are checked for expression of IL-11 by bioassay, immunoassay or RNA blotting and positive pools are subsequently selected for amplification by growth in increasing concentrations of MTX (sequential steps in 0.02, 0.2, 1.0 and 5 uM MTX) as described in Kaufman et al, *Mol. Cell Biol.*, 5:1750 (1983). The amplified lines are cloned, and biologically active IL-11 polypeptide expression is monitored by the T1165 assay. IL-11 polypeptide expression is expected to increase with increasing levels of MTX resistance.

In any of the expression systems described above, the resulting cell lines can be further amplified by appropriate drug selection, resulting cell lines recloned and the level of expression assessed using the T1165 assay described herein.

The IL-11 expressing CHO cell lines can be adapted to growth in serum-free medium. Homogeneous IL-11 can be isolated from conditioned medium from the cell line using methods familiar in the art, including techniques such as lectin-affinity chromatography, reverse phase HPLC, FPLC and the like.

EXAMPLE 11

Effect of IL-11 on Proliferation in Culture of Early Murine Progenitors

Methylcellulose cell cultures were established in 35 mm Lux suspension culture dishes (#5221R, Nunc, Inc. Naperville, Ill.).

5-Fluorouracil (5-FU) (Adria Laboratories, Columbia, Ohio) was administered intravenously through the tail veins of 10 to 15 week old female $BDF_1$ mice [ARS Sprague Dawley, Indianapolis, Ind.] at 150 mg/kg body weight [T. Suda et al, *J. Cell. Physiol.*, 117:308–318 (1983) and G. S. Hodgson et al, *Nature*, 281:381–382 (1979)]. Single cell suspensions were prepared from pooled femurs or spleens of three mice. Light density (<1,077) mononuclear cells were collected from the interface of Ficoll-Paque after centrifugation at 400 g. After overnight adherence of these cells to plastic dishes, nonadherent mononuclear (bone marrow and spleen) cells were harvested 2 and 5 days after 5-FU injection, respectively.

One ml of culture contained $2 \times 10^4$ marrow cells from normal mice, $5 \times 10^4$ marrow cells or $1 \times 10^6$ spleen cells from 5-FU-treated mice, α-medium (Flow Laboratories, Inc., McLean, Va.), 1.2% 1,500 cps methylcellulose (Fisher Scientific Co., Norcross, Ga.), 30% fetal calf serum (FCS) (Hyclone Laboratories, Inc., Logan, Utah), 1% deionized fraction V bovine serum albumin (BSA) (Sigma Chemical Co., St. Louis, Mo.), $1 \times 10^{-4}$M 2-mercaptoethanol (Eastman Organic Chemicals, Rochester, N.Y.) and hemopoietic factors. Dishes were incubated at 37° C. in a humidified atmosphere flushed with 5% $CO_2$. Except for megakaryocyte colonies, colonies consisting of 50 or more cells were scored on an inverted microscope on the specified day of incubation. Megakaryocyte colonies were scored when they contained four or more megakaryocytes. Abbreviations for colony types are as follows: GM, granulocyte/macrophage; Mast, mast cell colonies; E, erythroid bursts; M, megakaryocyte colonies; GMM, granulocyte/macrophage/megakaryocyte colonies [T. Nakahata et al, *J. Cell. Physiol.*, 111:239–246 (1982)]; GEMM, granulocyte/erythrocyte/macrophage/megakaryocyte colonies [T. Nakahata et al, cited above; and A. A. Fauser et al, *Blood*, 52:1243–1248 (1978)]; and B1, blast cell colonies [T. Nakahata et al, *Proc. Natl. Acad. Sci. USA*, 79:3843–3847 (1982); and T. Suda et al, cited above].

The hemopoietic potential of the blast cell colonies was determined by blast cell colony replating. Between days 5 and 15 of incubation, individual blast cell colonies containing 50 to 150 cells were picked with an Eppendorf pipet and replated in secondary methylcellulose cultures containing 2 U/ml human urinary erythropoietin (Ep) [activity of 370 U per mg, available M from Dr. Makoto Kawakita, Kumamoto University Medical School, Kumamoto, Japan], 1% (v/v) concentrated (×20) supernatant of cultures of WEHI-3 cells.

Blast cells were also used as pure target populations of hemopoietic cells to determine whether the observed effects of IL-11 were direct or due to the release of other factors. One million day-4 post-5-FU spleen cells were cultured in the presence of 100 U/ml of recombinant murine IL-3. IL-3 was conditioned by Chinese Hamster Ovary (CHO) cells that had been genetically engineered to produce murine IL-3 to high titer (approximately 30,000 U/ml). On day 8 of culture, individual blast cell colonies (between 50 to 150 cells) were picked from cultures, pooled, washed twice with medium and replated in secondary cultures each containing different combinations of factors.

Recombinant human IL-6 with specific activity of $4 \times 10^6$ U/mg protein was expressed in *E. coli*. IL-11 was medium conditioned (CM) by COS-1 cells transfected with cDNA encoding the murine plasmacytoma-stimulatory activity [S. R. Paul et al, *Proc. Natl. Acad. Sci. USA*, in press (1990)].

A. Colony Formation from Marrow Cells of Normal Mice

Colony formation from normal marrow cells was supported by IL-11. In the presence or absence of 2 U/ml Ep, IL-11 gave rise to colonies in a dose-dependent manner. A 1:100 dilution of IL-11 supported maximal colony formation. However, the total number of colonies detected on day 8 or day 16 of incubation with IL-11 was significantly fewer than in cultures with IL-3. The colonies found in IL-11-containing cultures were predominantly of the GM type, although some multilineage (GMM and GEMM) colonies were also observed. IL-11 in a 1:100 dilution supported formation of three blast cell colonies on day 16 of incubation.

B. Colony Formation from Marrow Cells of 5-FU-Treated Mice

Colony formation from marrow cells harvested two days after injection of 150 mg/kg 5-FU [T. Suda et al., cited above; and G. S. Hodgson et al., cited above] in cultures established in the presence of IL-11, IL-6, IL-3 singly and in various combinations was studied to determine whether IL-11 acts synergistically with IL-3 in supporting the proliferation of primitive progenitors.

Addition of IL-11 at final dilutions of 1:100 and 1:1,000 to an optimal concentration of IL-3 significantly enhanced colony formation. In particular, in the presence of a 1:100 dilution of IL-11 and IL-3 the kinetics of colony formation was accelerated as compared to that supported by the individual factors. The time course of colony formation as well as the total number of colonies supported were similar to those observed with the combination of IL-6 and IL-3. IL-11 alone in a 1:100 dilution supported scant colony formation after a long period of incubation. These results indicated that IL-11 enhances IL-3-dependent proliferation of primitive progenitors.

The effects of a combination of IL-11 and IL-6 on the kinetics of colony formation from day-2 post-5-FU marrow cells relative to the effects of individual synergistic factors were tested separately. IL-6 and IL-11 significantly accelerated IL-3-dependent colony formation. The effects of the combination of IL-6 and IL-11, however, did not differ from those of individual factors.

C. Serial Observations of Blast Cell Colony Development from Day-4 Post-5-FU Spleen Cells The growth rates of individual blast cell colonies were serially plotted through culture mapping studies. The results indicated that the synergistic effect of IL-11 results from a decrease in the time stem cells spend in the dormant state, an effect very similar to that observed with IL-6 or G-CSF because the growth rates were not statistically different in these culture systems.

D. Comparison of the Replating Potentials of Blast Cell Colonies

The proliferative potentials of blast cell colonies that respond to IL-11 and IL-6 were tested by replating experiments. Significant variations in the secondary replating efficiencies were seen among individual blast cell colonies as reported previously [K. Ikebuchi et al., *Blood*, 72:2007–2014 (1988)]. There was, however, no significant differences in the replating efficiencies of blast cell colonies grown in the three different primary culture conditions.

Similar to previous observations [K. Ikebuchi et al., cited above], the percentages of secondary GEMM colonies in secondary colonies and the incidences of secondary GEMM colonies per blast cell colonies were significantly higher from the primary blast cell colonies identified in cultures containing IL-11 or IL-6 than those seen in cultures containing IL-3 alone. There were no significant differences in these parameters between cultures containing IL-11 plus IL-3 and cultures containing IL-6 plus IL-3.

These results indicated that the synergistic activities of IL-11 and IL-6 are similar and that the increases in the incidences of secondary GEMM colonies may be due to shortening of the G. period of stem cells during blast cell colony formation [K. Ikebuchi et al., cited above].

E. Replating Studies of Pooled Blast Cells

Target cells obtained by pooling blast cells from early stages of cultures supported by IL-3 were used to compare the direct effects of IL-11 and IL-6 on GM colony formation. Pooled blast cells are devoid of stromal cells and express very high replating efficiencies.

Blast cell colonies containing 50 to 150 cells identified in cultures containing IL-3 were picked and pooled, and were replated in secondary cultures containing IL-11, IL-6 or IL-3 in the presence of 2 U/ml Ep. These date indicate that at least 70% of the blast cells are hemopoietic progenitors.

While the combination of IL-3 and Ep supported formation of a variety of single lineage and multilineage colonies, IL-11 and Ep supported the formation of only macrophage colonies. The combination of IL-6 and Ep supported formation of a similar number of pure macrophage colonies but also neutrophil/macrophage colonies. The macrophage colonies supported by IL-11 were smaller than the macrophage colonies supported by IL-6.

These results indicated that IL-11 and IL-6 interact with overlapping but different progenitor subsets and that IL-11 preferentially supports the macrophage progenitor population.

F. The Effects of Neutralizing Anti-IL-6 Antibody on the Synergistic Effects of IL-11

In order to confirm that the direct colony-supporting ability between IL-11 and IL-6 was not a result of the crude nature of the Cos cell CM, neutralizing anti-IL-6 antibody, which is known to inhibit Cos-derived IL-6, was used to study the synergistic effects of IL-11 and IL-6 on IL3-dependent proliferation from dormant progenitors.

In the presence of IL-6 or IL-11 and in the absence of antibodies, colony development from day-4-post-5-FU spleen cells was significantly hastened as indicated by the number of colonies on day 8. When anti-IL-6 antibody was present, the synergistic effects of IL-6 were completely abrogated while the effects of IL-11 were not. The effects of the antibody persisted until day 16. These results excluded the possibility that the apparent synergistic effects in Cos cell CM were mediated by IL-6.

The conditioned medium (CM) of COS cells transfected with IL-11 cDNA has been found to augment IL-3-dependent proliferation of multipotential progenitors in culture, an activity originally associated with IL-6. The mechanism of the augmentation appears to be shortening of the G. period of dormant stem cells.

The foregoing descriptions detail presently preferred embodiments of the invention. Numerous modifications and variations in practice of this invention are expected to occur to those skilled in the art. Such modifications and variations are encompassed within the following claims.

We claim:

1. An IL-11 produced by a method comprising the steps of:

(a) culturing a host cell transformed with a DNA molecule which hybridizes under stringent wash conditions of 0.1×SSC at 65° C. to a complement of the DNA encoding an IL-11 having an amino acid sequence comprising amino acids 22 through 199 of SEQ ID NO:2; and (b) recovering said IL-11.

2. Purified IL-11 encoded by an isolated DNA molecule comprising a DNA molecule selected from the group consisting of the DNA molecules of ATCC deposit numbers 68284 and 68172.

3. Purified IL-11 encoded by a DNA molecule which hybridizes under stringent wash conditions of 0.1×SSC at 65° C. to a complement of the DNA encoding an IL-11 having an amino acid sequence comprising amino acids 22 through 199 of SEQ ID NO:2.

4. A pharmaceutical composition comprising IL-11 according to claim 3 in admixture with a pharmaceutically acceptable vehicle.

5. The composition of claim 4, wherein said composition further comprises at least one additional cytokine selected from the group consisting of an interleukin, GM-CSF (Granulocyte Macrophage-Colony Stimulating Factor), G-CSF (Granulocyte-Colony Stimulating Factor), M-CSF (Macrophage-Colony Stimulating Factor), an interferon, Meg-CSF (Negakaryocyte-Colony Stimulating Factor), MIF (Macrophage Inhibitory Factor), LIF(Leukemia Inhibitory Factor), TNF(Tissue Necrosis Factor), and EPO (erythropoietin).

6. The composition of claim 5, wherein said cytokine is G-CSF.

7. A pharmaceutical composition comprising IL-11 according to claim 3 and a member selected from the group consisting of a cytokine, an hematopoietin, and a growth factor.

8. The composition according to claim 7 wherein said cytokine is selected from the group consisting of an interleukin, GM-CSF, G-CSF, M-CSF, an interferon, Meg-CSF, MIF, LIF, TNF, and EPO.

9. The composition according to claim 8 wherein said cytokine is a member selected from the group consisting of IL-3 and IL-6.

10. A method for accelerating wound healing comprising administering an effective amount of IL-11 according to claim 3.

11. A method for increasing platelet formation comprising administering IL-11 according to claim 3.

12. An injectable pharmaceutical composition for increasing platelet formation comprising an aqueous solution of IL-11 according to claim 3 and a pharmaceutically acceptable carrier.

13. A method for increasing immune cell formation comprising administering IL-11 according to claim 3.

14. The method according to claim 13 further comprising administering simultaneously or sequentially with said IL-11 a member selected from the group consisting of an hematopoietin, a cytokine, and a growth factor.

15. The method according to claim 14 wherein said cytokine is a member selected from the group consisting of IL-3 and IL-6.

16. A method for increasing hematopoietic cell formation comprising administering IL-11 according to claim 3.

17. The method according to claim 16 further comprising administering simultaneously or sequentially with said IL-11 a member selected from the group consisting of an hematopoietin, a cytokine, and a growth factor.

18. The method according to claim 17 wherein said cytokine is a member selected from the group consisting of IL-3 and IL-6.

19. A method for treating infections comprising administering IL-11 according to claim 3.

20. The method of claim 19, wherein said infection is bacterial.

21. The method of claim 19, wherein said IL-11 is administered intravenously.

22. A pharmaceutical composition for treating infections comprising an aqueous solution of IL-11 according to claim 3 and a pharmaceutically acceptable carrier.

23. A pharmaceutical composition for topical administration for treating infections comprising IL-11 according to claim 3 and a pharmaceutically acceptable carrier.

24. A method of modulating the function of a cytokine comprising administering IL-11 encoded by a DNA molecule which hybridizes under stringent wash conditions of 0.1×SSC at 65° C. to a complement of the DNA encoding an IL-11 having an amino acid sequence comprising amino acids 22 through 199 of SEQ ID NO:2.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 1100 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO -continued ( i x ) FEATURE:
    ( A ) NAME/KEY: CDS
    ( B ) LOCATION: 73..669

( x i ) SEQUENCE DESCRIPTION: SEQ ID NO:1:

```
GGGAAGGTGG  AAGGGTTAAA  GGCCCCCGGC  TCCCTGCCCC  CTGCCCTGGG  GAACCCCTGG           60

CCCTGCGGGG AC ATG AAC TGT GTT TGC CGC CTG GTC CTG GTC GTG CTG                   108
              Met Asn Cys Val Cys Arg Leu Val Leu Val Val Leu
                1               5                  10

AGC CTG TGG CCA GAT ACA GCT GTT GCC CCT GGG CCA CCA CCT GGC TCC                 156
Ser Leu Trp Pro Asp Thr Ala Val Ala Pro Gly Pro Pro Pro Gly Ser
         15                  20                  25

CCT CGA GCT TCC CCA GAC CCT CGG GCC GAG CTG GAC AGC ACC GTG CTC                 204
Pro Arg Ala Ser Pro Asp Pro Arg Ala Glu Leu Asp Ser Thr Val Leu
     30              35                  40

CTG ACC CGC TCT CTC CTG GAG GAC ACG CGG CAG CTG ACT ATA CAG CTG                 252
Leu Thr Arg Ser Leu Leu Glu Asp Thr Arg Gln Leu Thr Ile Gln Leu
 45                  50                  55                  60

AAG GAC AAA TTC CCA GCT GAC GGG GAC CAC AAC CTG GAT TCC CTG CCC                 300
Lys Asp Lys Phe Pro Ala Asp Gly Asp His Asn Leu Asp Ser Leu Pro
                 65                  70                  75

ACC CTG GCC ATG AGC GCG GGG GCA CTG GGA GCT CTA CAG CTC CCG AGT                 348
Thr Leu Ala Met Ser Ala Gly Ala Leu Gly Ala Leu Gln Leu Pro Ser
                 80                  85                  90

GTG CTG ACA AGG CTG CGA GCG GAC CTA CTG TCC TAC CTG CGG CAT GTG                 396
Val Leu Thr Arg Leu Arg Ala Asp Leu Leu Ser Tyr Leu Arg His Val
             95                 100                 105

CAG TGG CTG CGT CGG GCA ATG GGC TCT TCC CTG AAG ACC CTG GAG CCT                 444
Gln Trp Leu Arg Arg Ala Met Gly Ser Ser Leu Lys Thr Leu Glu Pro
    110                 115                 120

GAG CTG GGC ACC CTG CAG ACC CGG CTG GAC CGG CTG CTG CGC CGG CTG                 492
Glu Leu Gly Thr Leu Gln Thr Arg Leu Asp Arg Leu Leu Arg Arg Leu
125                 130                 135                 140

CAG CTC CTG ATG TCC CGC CTG GCC CTG CCC CAG CTG CCC CCA GAC CCG                 540
Gln Leu Leu Met Ser Arg Leu Ala Leu Pro Gln Leu Pro Pro Asp Pro
                145                 150                 155

CCG GCG CCC CCG CTG GCG CCC CCC TCC TCA ACC TGG GGG GGC ATC AGG                 588
Pro Ala Pro Pro Leu Ala Pro Pro Ser Ser Thr Trp Gly Gly Ile Arg
                160                 165                 170

GCC GCC CAC GCC ATC CTG GGG GGG CTG CAC CTG ACA CTT GAC TGG GCC                 636
Ala Ala His Ala Ile Leu Gly Gly Leu His Leu Thr Leu Asp Trp Ala
            175                 180                 185

GTG AGG GGG CTA CTG CTG CTG AAG ACT CGG CTG TGACCCGAGG CCCAGAGCCA               689
Val Arg Gly Leu Leu Leu Leu Lys Thr Arg Leu
        190                 195

CCACCGTCCT  TCCAAAGCCA  CATCTTATTT  ATTTATTTAT  TTCGGTACTG  GGGGCGAAAC          749

AGCCAGGTGA  TCCCCCTGCC  TTTAGCTCCC  CCTAGTTAGA  GACAGTCCTT  CCGTGAGGCT          809

GGGGGGCATC  TGTGCCTTAT  TTATACTTAT  TTATTTCAGG  AGCGGGGTG   GGCTCCTGGG          869

TCCCCGAGGA  GGAGGGAGCT  GGGGTCCCGG  ATTCTTGTGT  CCACAGACTT  CTGCCCTGGC          929

TCCTCCCCCT  CGAGGCCTGG  GCAGGAATAC  ATACTATTTA  TTTAAGCAAT  TACTTTTCAT          989

GTTGGGGTGG  GGAGGGAGGG  GAAAGGGAAG  CCTGGGTTTT  TGTACAAAAA  TGTGAGAAAC         1049

CTTTGTGAGA  CGGAGAACAA  GGAATTAAAT  GTGTCATACA  TAAAAAAAAA  A                  1100
```

( 2 ) INFORMATION FOR SEQ ID NO:2:

( i ) SEQUENCE CHARACTERISTICS:
        ( A ) LENGTH: 199 amino acids
        ( B ) TYPE: amino acid ( D ) TOPOLOGY: linear ( i i ) MOLECULE TYPE: protein ( x i ) SEQUENCE DESCRIPTION: SEQ ID NO:2:

| Met | Asn | Cys | Val | Cys | Arg | Leu | Val | Leu | Val | Val | Leu | Ser | Leu | Trp | Pro |
|---|---|---|---|---|---|---|---|---|---|---|---|---|---|---|---|
| 1 | | | | 5 | | | | | 10 | | | | | 15 | |

| Asp | Thr | Ala | Val | Ala | Pro | Gly | Pro | Pro | Pro | Gly | Ser | Pro | Arg | Ala | Ser |
|---|---|---|---|---|---|---|---|---|---|---|---|---|---|---|---|
| | | | 20 | | | | | 25 | | | | | 30 | | |

| Pro | Asp | Pro | Arg | Ala | Glu | Leu | Asp | Ser | Thr | Val | Leu | Leu | Thr | Arg | Ser |
|---|---|---|---|---|---|---|---|---|---|---|---|---|---|---|---|
| | | | 35 | | | | | 40 | | | | | 45 | | |

| Leu | Leu | Glu | Asp | Thr | Arg | Gln | Leu | Thr | Ile | Gln | Leu | Lys | Asp | Lys | Phe |
|---|---|---|---|---|---|---|---|---|---|---|---|---|---|---|---|
| | | 50 | | | | | 55 | | | | | 60 | | | |

| Pro | Ala | Asp | Gly | Asp | His | Asn | Leu | Asp | Ser | Leu | Pro | Thr | Leu | Ala | Met |
|---|---|---|---|---|---|---|---|---|---|---|---|---|---|---|---|
| 65 | | | | | 70 | | | | | 75 | | | | | 80 |

| Ser | Ala | Gly | Ala | Leu | Gly | Ala | Leu | Gln | Leu | Pro | Ser | Val | Leu | Thr | Arg |
|---|---|---|---|---|---|---|---|---|---|---|---|---|---|---|---|
| | | | | 85 | | | | | 90 | | | | | 95 | |

| Leu | Arg | Ala | Asp | Leu | Leu | Ser | Tyr | Leu | Arg | His | Val | Gln | Trp | Leu | Arg |
|---|---|---|---|---|---|---|---|---|---|---|---|---|---|---|---|
| | | | 100 | | | | | 105 | | | | | 110 | | |

| Arg | Ala | Met | Gly | Ser | Ser | Leu | Lys | Thr | Leu | Glu | Pro | Glu | Leu | Gly | Thr |
|---|---|---|---|---|---|---|---|---|---|---|---|---|---|---|---|
| | | | 115 | | | | | 120 | | | | | 125 | | |

| Leu | Gln | Thr | Arg | Leu | Asp | Arg | Leu | Leu | Arg | Arg | Leu | Gln | Leu | Leu | Met |
|---|---|---|---|---|---|---|---|---|---|---|---|---|---|---|---|
| | | 130 | | | | | 135 | | | | | 140 | | | |

| Ser | Arg | Leu | Ala | Leu | Pro | Gln | Leu | Pro | Pro | Asp | Pro | Pro | Ala | Pro | Pro |
|---|---|---|---|---|---|---|---|---|---|---|---|---|---|---|---|
| 145 | | | | | 150 | | | | | 155 | | | | | 160 |

| Leu | Ala | Pro | Pro | Ser | Ser | Thr | Trp | Gly | Gly | Ile | Arg | Ala | Ala | His | Ala |
|---|---|---|---|---|---|---|---|---|---|---|---|---|---|---|---|
| | | | | 165 | | | | | 170 | | | | | 175 | |

| Ile | Leu | Gly | Gly | Leu | His | Leu | Thr | Leu | Asp | Trp | Ala | Val | Arg | Gly | Leu |
|---|---|---|---|---|---|---|---|---|---|---|---|---|---|---|---|
| | | | 180 | | | | | 185 | | | | | 190 | | |

| Leu | Leu | Leu | Lys | Thr | Arg | Leu |
|---|---|---|---|---|---|---|
| | | 195 | | | | |

( 2 ) INFORMATION FOR SEQ ID NO:3:

( i ) SEQUENCE CHARACTERISTICS:
        ( A ) LENGTH: 1208 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 138..734

( x i ) SEQUENCE DESCRIPTION: SEQ ID NO:3:

```
GGCTCAGGGC ACATGCCTCC CCTCCCCAGG CCGCGGCCCA GCTGACCCTC GGGGCTCCCC        60

CGGCAGCGGA CAGGGAAGGG TTAAAGGCCC CCGGCTCCCT GCCCCCTGCC CTGGGGAACC       120

CCTGGCCCTG TGGGGAC ATG AAC TGT GTT TGC CGC CTG GTC CTG GTC GTG         170
                Met Asn Cys Val Cys Arg Leu Val Leu Val Val
                 1               5                  10

CTG AGC CTG TGG CCA GAT ACA GCT GTC GCC CCT GGG CCA CCA CCT GGC         218
Leu Ser Leu Trp Pro Asp Thr Ala Val Ala Pro Gly Pro Pro Pro Gly
            15                  20                  25

CCC CCT CGA GTT TCC CCA GAC CCT CGG GCC GAG CTG GAC AGC ACC GTG         266
Pro Pro Arg Val Ser Pro Asp Pro Arg Ala Glu Leu Asp Ser Thr Val
```

|     |     |     |     |     | 30  |     |     |     |     | 35  |     |     |     |     | 40  |     |     |     |     |     |
|-----|-----|-----|-----|-----|-----|-----|-----|-----|-----|-----|-----|-----|-----|-----|-----|-----|-----|-----|-----|-----|
| CTC | CTG | ACC | CGC | TCT | CTC | CTG | GCG | GAC | ACG | CGG | CAG | CTG | GCT | GCA | CAG | 314 |
| Leu | Leu | Thr | Arg | Ser | Leu | Leu | Ala | Asp | Thr | Arg | Gln | Leu | Ala | Ala | Gln |     |
|     |     | 45  |     |     |     |     | 50  |     |     |     |     | 55  |     |     |     |     |

| CTG | AGG | GAC | AAA | TTC | CCA | GCT | GAC | GGG | GAC | CAC | AAC | CTG | GAT | TCC | CTG | 362 |
| Leu | Arg | Asp | Lys | Phe | Pro | Ala | Asp | Gly | Asp | His | Asn | Leu | Asp | Ser | Leu |     |
| 60  |     |     |     |     | 65  |     |     |     |     | 70  |     |     |     |     | 75  |     |

| CCC | ACC | CTG | GCC | ATG | AGT | GCG | GGG | GCA | CTG | GGA | GCT | CTA | CAG | CTC | CCA | 410 |
| Pro | Thr | Leu | Ala | Met | Ser | Ala | Gly | Ala | Leu | Gly | Ala | Leu | Gln | Leu | Pro |     |
|     |     |     |     | 80  |     |     |     |     | 85  |     |     |     |     | 90  |     |     |

| GGT | GTG | CTG | ACA | AGG | CTG | CGA | GCG | GAC | CTA | CTG | TCC | TAC | CTG | CGG | CAC | 458 |
| Gly | Val | Leu | Thr | Arg | Leu | Arg | Ala | Asp | Leu | Leu | Ser | Tyr | Leu | Arg | His |     |
|     |     |     | 95  |     |     |     |     | 100 |     |     |     |     | 105 |     |     |     |

| GTG | CAG | TGG | CTG | CGC | CGG | GCA | GGT | GGC | TCT | TCC | CTG | AAG | ACC | CTG | GAG | 506 |
| Val | Gln | Trp | Leu | Arg | Arg | Ala | Gly | Gly | Ser | Ser | Leu | Lys | Thr | Leu | Glu |     |
|     |     | 110 |     |     |     |     | 115 |     |     |     |     | 120 |     |     |     |     |

| CCC | GAG | CTG | GGC | ACC | CTG | CAG | GCC | CGA | CTG | GAC | CGG | CTG | CTG | CGC | CGG | 554 |
| Pro | Glu | Leu | Gly | Thr | Leu | Gln | Ala | Arg | Leu | Asp | Arg | Leu | Leu | Arg | Arg |     |
|     | 125 |     |     |     |     | 130 |     |     |     |     | 135 |     |     |     |     |     |

| CTG | CAG | CTC | CTG | ATG | TCC | CGC | CTG | GCC | CTG | CCC | CAG | CCA | CCC | CCG | GAC | 602 |
| Leu | Gln | Leu | Leu | Met | Ser | Arg | Leu | Ala | Leu | Pro | Gln | Pro | Pro | Pro | Asp |     |
| 140 |     |     |     | 145 |     |     |     |     | 150 |     |     |     |     | 155 |     |     |

| CCG | CCG | GCG | CCC | CCG | CTG | GCG | CCC | CCC | TCC | TCA | GCC | TGG | GGG | GGC | ATC | 650 |
| Pro | Pro | Ala | Pro | Pro | Leu | Ala | Pro | Pro | Ser | Ser | Ala | Trp | Gly | Gly | Ile |     |
|     |     |     |     | 160 |     |     |     |     | 165 |     |     |     |     | 170 |     |     |

| AGG | GCC | GCC | CAC | GCC | ATC | CTG | GGG | GGG | CTG | CAC | CTG | ACA | CTT | GAC | TGG | 698 |
| Arg | Ala | Ala | His | Ala | Ile | Leu | Gly | Gly | Leu | His | Leu | Thr | Leu | Asp | Trp |     |
|     |     |     | 175 |     |     |     |     | 180 |     |     |     |     | 185 |     |     |     |

| GCC | GTG | AGG | GGA | CTG | CTG | CTG | CTG | AAG | ACT | CGG | CTG | TGACCCGGGG |     |     |     | 744 |
| Ala | Val | Arg | Gly | Leu | Leu | Leu | Leu | Lys | Thr | Arg | Leu |     |     |     |     |     |
|     |     | 190 |     |     |     |     |     | 195 |     |     |     |     |     |     |     |     |

| CCCAAAGCCA | CCACCGTCCT | TCCAAAGCCA | GATCTTATTT | ATTTATTTAT | TTCAGTACTG | 804  |
| GGGGCGAAAC | AGCCAGGTGA | TCCCCCCGCC | ATTATCTCCC | CCTAGTTAGA | GACAGTCCTT | 864  |
| CCGTGAGGCC | TGGGGGACAT | CTGTGCCTTA | TTTATACTTA | TTTATTTCAG | GAGCAGGGGT | 924  |
| GGGAGGCAGG | TGGACTCCTG | GGTCCCCGAG | GAGGAGGGGA | CTGGGGTCCC | GGATTCTTGG | 984  |
| GTCTCCAAGA | AGTCTGTCCA | CAGACTTCTG | CCCTGGCTCT | TCCCCATCTA | GGCCTGGGCA | 1044 |
| GGAACATATA | TTATTTATTT | AAGCAATTAC | TTTTCATGTT | GGGGTGGGGA | CGGAGGGGAA | 1104 |
| AGGGAAGCCT | GGGTTTTTGT | ACAAAAATGT | GAGAAACCTT | TGTGAGACAG | AGAACAGGGA | 1164 |
| ATTAAATGTG | TCATACATAT | CCAAAAAAAA | AAAAAAAAA  | AAAA       |            | 1208 |

( 2 ) INFORMATION FOR SEQ ID NO:4:

( i ) SEQUENCE CHARACTERISTICS:
        ( A ) LENGTH: 199 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Met | Asn | Cys | Val | Cys | Arg | Leu | Val | Leu | Val | Val | Leu | Ser | Leu | Trp | Pro |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Asp | Thr | Ala | Val | Ala | Pro | Gly | Pro | Pro | Gly | Pro | Pro | Arg | Val | Ser |
|-----|-----|-----|-----|-----|-----|-----|-----|-----|-----|-----|-----|-----|-----|-----|
|     |     |     | 20  |     |     |     |     | 25  |     |     |     | 30  |     |     |

| Pro | Asp | Pro | Arg | Ala | Glu | Leu | Asp | Ser | Thr | Val | Leu | Leu | Thr | Arg | Ser |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Leu | Leu | Ala | Asp | Thr | Arg | Gln | Leu | Ala | Ala | Gln | Leu | Arg | Asp | Lys | Phe |

|  |  |  |  |  | 50 |  |  |  |  | 55 |  |  |  |  | 60 |  |
|---|---|---|---|---|---|---|---|---|---|---|---|---|---|---|---|---|
| Pro 65 | Ala | Asp | Gly | Asp | His 70 | Asn | Leu | Asp | Ser | Leu 75 | Pro | Thr | Leu | Ala | Met 80 | |
| Ser | Ala | Gly | Ala | Leu 85 | Gly | Ala | Leu | Gln | Leu 90 | Pro | Gly | Val | Leu | Thr 95 | Arg | |
| Leu | Arg | Ala | Asp 100 | Leu | Leu | Ser | Tyr | Leu 105 | Arg | His | Val | Gln | Trp 110 | Leu | Arg | |
| Arg | Ala | Gly 115 | Gly | Ser | Ser | Leu | Lys 120 | Thr | Leu | Glu | Pro | Glu 125 | Leu | Gly | Thr | |
| Leu | Gln 130 | Ala | Arg | Leu | Asp | Arg 135 | Leu | Leu | Arg | Arg | Leu 140 | Gln | Leu | Leu | Met | |
| Ser 145 | Arg | Leu | Ala | Leu | Pro 150 | Gln | Pro | Pro | Asp 155 | Pro | Pro | Ala | Pro 160 | Pro | | |
| Leu | Ala | Pro | Pro | Ser 165 | Ser | Ala | Trp | Gly | Gly 170 | Ile | Arg | Ala | Ala | His 175 | Ala | |
| Ile | Leu | Gly | Gly 180 | Leu | His | Leu | Thr | Leu 185 | Asp | Trp | Ala | Val | Arg 190 | Gly | Leu | |
| Leu | Leu | Leu 195 | Lys | Thr | Arg | Leu | | | | | | | | | | |